(12) United States Patent
He et al.

(10) Patent No.: US 12,290,329 B2
(45) Date of Patent: May 6, 2025

(54) SURGICAL ROBOT AND SURGICAL INSTRUMENT

(71) Applicant: SHANGHAI MICROPORT MEDBOT (GROUP) CO., LTD., Shanghai (CN)

(72) Inventors: Yuyuan He, Shanghai (CN); Chao He, Shanghai (CN); Youkun Jiang, Shanghai (CN)

(73) Assignee: SHANGHAI MICROPORT MEDBOT (GROUP) CO., LTD., Shanghai (CN)

( * ) Notice: Subject to any disclaimer, the term of this patent is extended or adjusted under 35 U.S.C. 154(b) by 660 days.

(21) Appl. No.: 17/635,256

(22) PCT Filed: Aug. 13, 2020

(86) PCT No.: PCT/CN2020/108986
§ 371 (c)(1),
(2) Date: Feb. 14, 2022

(87) PCT Pub. No.: WO2021/027894
PCT Pub. Date: Feb. 18, 2021

(65) Prior Publication Data
US 2022/0280253 A1    Sep. 8, 2022

(30) Foreign Application Priority Data
Aug. 15, 2019   (CN) .......................... 201910754526.1

(51) Int. Cl.
*A61B 34/00* (2016.01)
*A61B 34/30* (2016.01)
*A61B 17/29* (2006.01)

(52) U.S. Cl.
CPC .............. *A61B 34/71* (2016.02); *A61B 34/30* (2016.02); *A61B 2017/2929* (2013.01); *A61B 2017/2944* (2013.01); *A61B 2034/715* (2016.02)

(58) Field of Classification Search
CPC . A61B 34/71; A61B 34/30; A61B 2017/2929; A61B 2017/2944; A61B 2034/301; A61B 2034/305–306
See application file for complete search history.

(56) References Cited

U.S. PATENT DOCUMENTS

2009/0171374 A1* 7/2009 Omori .................... A61B 34/71
606/130
2010/0004508 A1* 1/2010 Naito ..................... A61B 34/37
600/141
(Continued)

FOREIGN PATENT DOCUMENTS

CN          102119872 B      11/2012
CN          105212987 A       1/2016
(Continued)

*Primary Examiner* — Brigid K Byrd
(74) *Attorney, Agent, or Firm* — MUNCY, GEISSLER, OLDS & LOWE, P.C.

(57) ABSTRACT

A surgical robot and a surgical instrument are disclosed. The surgical instrument includes a wire transmission and an end section. The wire transmission includes a base and n transmission modules each including at least one end drive shaft, two traction elements and two guide pulleys. Each of the guide pulleys comprises a groove for receiving therein a respective one of the traction elements. The groove has a plane of rotation, an entry point of tangency and an exit point of tangency. An angle between the traction element defined by the end drive shaft and the entry point of tangency and the plane of rotation is in the range of 0-0.2°. Projections of all the traction elements at the respective exit points of tangency on the proximal end portion are circumferentially (Continued)

arranged in the same order as the circumferential arrangement of the respective through holes.

20 Claims, 18 Drawing Sheets

(56) References Cited

U.S. PATENT DOCUMENTS

| | | | | |
|---|---|---|---|---|
| 2010/0160929 A1* | 6/2010 | Rogers | ................... | A61B 34/30 |
| | | | | 606/130 |
| 2010/0331857 A1 | 12/2010 | Doyle et al. | | |
| 2020/0237466 A1* | 7/2020 | Lee | ................... | A61B 17/2909 |
| 2021/0196416 A1* | 7/2021 | Betsugi | ................... | A61B 34/35 |

FOREIGN PATENT DOCUMENTS

| | | | |
|---|---|---|---|
| CN | 106109019 | A | 11/2016 |
| CN | 106308933 | A | 1/2017 |
| CN | 106806023 | A | 6/2017 |
| CN | 110368092 | A | 10/2019 |
| CN | 211156230 | U | 8/2020 |
| WO | WO-2017/063472 | A1 | 4/2017 |

* cited by examiner

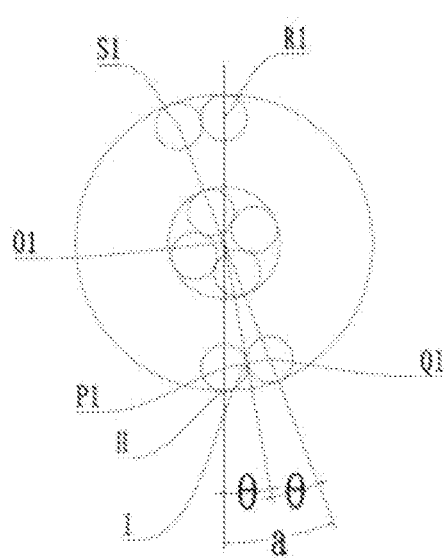 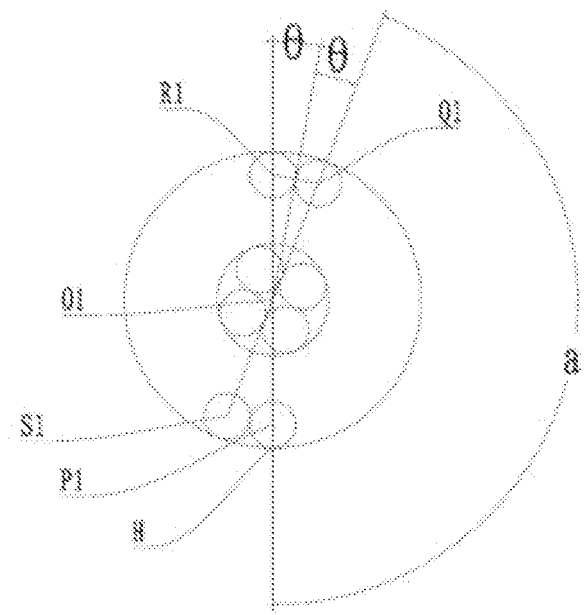
Fig. 26(A)　　　　　　　　Fig. 26(B)
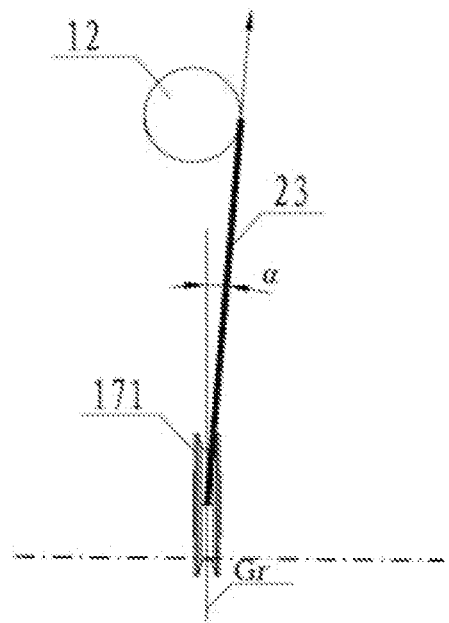
Fig. 27

SURGICAL ROBOT AND SURGICAL INSTRUMENT

TECHNICAL FIELD

The present invention relates to the technical field of surgical instruments and, more particularly, to a surgical robot and a surgical instrument.

BACKGROUND

In recent years, with the increasing application and development of robot-related technologies, in particular of computing technology, more and more importance is being attached to the role of surgical robots in clinical practice. Among such surgical robots, minimally invasive systems can relieve surgeons from strenuous physical labor by intervention while achieving precision surgery, and result in less trauma and bleeding, reduced postoperative infections and faster postoperative recovery, of patients. For these minimally invasive surgical robot systems, how well the surgical instruments they use are designed directly determines their success, and the performance of the surgical instruments is critical to the systems' performance.

To our knowledge, a surgical instrument disclosed in Chinese Patent Publication No. CN105212987A has 3 degrees of freedom at its one end enabled by 6 transmission cables and 9 guide pulleys in a gearbox for guiding the cables. However, this design is associated with a number of drawbacks. A first drawback is that the use of the pulleys tends to lead to reduced transmission efficiency, and the more pulleys are used, the greater an adverse effect will be exerted on transmission efficiency. For the same load to be driven, lower transmission efficiency means higher required power and hence generally a larger and heavier driving module (e.g., a motor) required to provide the power, which is not conducive to the overall surgical robot performance. A second drawback is that at least one of the guide pulleys is oriented at an angle of deflection from the running direction of the cable that it guides. With this arrangement, the cable will exert a lateral pressure on the guide pulley, causing lateral friction and increased resistance in the transmission chain. Moreover, when the angle of deflection is too large, the cable may accidentally fall off from the guide pulley. Further, the cable may frequently collide and rub against a groove surface of the pulley and thus shorten its life. A third drawback is that the 6 cables are collectively passed through a rod of the instrument, where, however, they may cross one another. When the end of the instrument is moving, the mutually crossing cables may heavily push and rub against one another, which is detrimental to transmission performance of the surgical instrument.

Therefore, there exists a need for a surgical instrument with improved performance.

SUMMARY OF THE INVENTION

It is an object of the present invention to overcome one or more of the above-described problems with the conventional surgical instrument, i.e., a large angle of deflection of at least one guide pulley from the cable that it guides and crossing and rubbing among cables, by presenting a novel surgical robot and surgical instrument.

In order to overcome at least one of the above-described problems, the present invention provides a surgical instrument comprising a wire transmission and an end section, the wire transmission comprising a base and n transmission modules, each of the transmission modules comprising an end drive shaft, two traction elements and two guide pulleys, where n is a natural number, the end section having at least n degrees of freedom, the end section comprising a proximal end portion provided with 2n circumferentially arranged through holes, the end drive shaft rotatably disposed on the base and configured to drive the end section to move via the two traction elements, in an $i^{th}$ one of the transmission modules, $j^{th}$ and $(j+1)^{th}$ traction elements proximally wound on an $i^{th}$ end drive shaft in opposite directions, the $j^{th}$ and $(j+1)^{th}$ traction elements distally guided by the $j^{th}$ and $(j+1)^{th}$ guide pulleys toward $j^{th}$ and $(j+1)^{th}$ ones of the through holes, respectively, and then passed through the $j^{th}$ and $(j+1)^{th}$ through holes, respectively, where i is a natural number in a range from 1 to n, and $j=2i-1$, each of the guide pulleys comprising a groove for receiving therein a respective one of the traction elements, the groove having a plane of rotation, an entry point of tangency and an exit point of tangency, the respective traction element configured to enter the guide pulley at the entry point of tangency and leave the guide pulley at the exit point of tangency, the guide pulley configured so that an angle between the plane of rotation and the traction element defined by the end drive shaft and the entry point of tangency is in a range of 0-0.2°, projections of all the traction elements at the respective exit points of tangency on the proximal end portion circumferentially arranged in a same order as a circumferential arrangement of the respective through holes on the proximal end portion.

Optionally, the end section may further have an axis line extending from a proximal end to a distal end thereof, wherein the guide pulley is further configured so that an angle between the axis line and the traction element defined by the exit point of tangency and a respective one of the through holes is in a range of 0-5°.

Optionally, the guide pulley may be further configured so that the angle between the axis line and the traction element defined by the exit point of tangency and the respective through hole is in a range of 0-1.5°.

Optionally, the $i^{th}$ end drive shaft may be connected to the $j^{th}$ traction element at a $j^{th}$ junction, and the traction element between the $j^{th}$ junction and the entry point of tangency of the $j^{th}$ guide pulley forms an angle in a range of 0-10° with the base, wherein the $i^{th}$ end drive shaft may be connected to the $(j+1)$th traction element at a $(j+1)$-th junction and forms between the $(j+1)^{th}$ junction and the entry point of tangency of the $(j+1)^{th}$ guide pulley forms an angle in a range of 0-10° with the base.

Optionally, every two of the traction elements may extend parallel to each other or in different planes between their junctions and the respective entry points of tangency.

Optionally, the surgical instrument may further comprise a rod drive shaft and a rod. The rod may be detachably or fixedly coupled to the end section and configured to drive the rod to spin.

Optionally, the end section may have at least three degrees of freedom, wherein the wire transmission comprises a first transmission module, a second transmission module and a third transmission module, each of the first, second and third transmission modules configured to drive the end section to move in a respective one of the degrees of freedom, the first transmission module comprising a first end drive shaft, a first traction element, a second traction element, a first guide pulley and a second guide pulley, the second transmission module comprising a second end drive shaft, a third traction element, a fourth traction element, a third guide pulley and a fourth guide pulley, the third transmission module comprising a third end drive shaft, a fifth traction element, a sixth traction element, a fifth guide pulley and a sixth guide pulley, and wherein the first, second, third, fourth, fifth and sixth traction elements correspond to the first, second, third, fourth, fifth and sixth guide pulleys, respectively.

Optionally, the end section may further comprise an end effector, the end effector comprising an effector base, a first openable and closable plate member and a second openable and closable plate member, the first and second openable and closable plate members both rotatably coupled to the effector base and thus providing at least two degrees of opening and closing freedom, the effector base rotatably coupled to the proximal end portion and thus providing at least one degree of swing freedom, wherein the first transmission module is configured to drive the first openable and closable plate member to move, the second transmission module is configured to drive the second openable and closable plate member to move, and the third transmission module is configured to drive the effector base to move relative to the proximal end portion.

Optionally, the through holes on the proximal end portion may include a first through hole, a second through hole, a third through hole, a fourth through hole, a fifth through hole and a sixth through hole for constraining extension of the first traction element, the second traction element, the third traction element, the fourth traction element, the fifth traction element and the sixth traction element, respectively,
  wherein an axis of rotation of the first and second openable and closable plate members is not parallel to an axis of rotation of the effector base, and
  wherein the fifth through hole, the third through hole, the first through hole, the sixth through hole, the second through hole and the fourth through hole are circumferentially arranged around a center of the proximal end portion.

Optionally, the fifth through hole may be symmetrical to the sixth through hole with respect to the center of the proximal end portion, wherein the third through hole is symmetrical to the second through hole with respect to the center of the proximal end portion, and the first through hole is symmetrical to the fourth through hole with respect to the center of the proximal end portion.

Optionally, the first guide pulley, the second guide pulley, the third guide pulley, the fourth guide pulley, the fifth guide pulley and the sixth guide pulley may have a first exit point of tangency, a second exit point of tangency, a third exit point of tangency, a fourth exit point of tangency, a fifth exit point of tangency and a sixth exit point of tangency, respectively,
  wherein the first traction element is projected at the first exit point of tangency onto the proximal end portion as a first projection,
  the second traction element at the second exit point of tangency onto the proximal end portion as a second projection,
  the third traction element at the third exit point of tangency onto the proximal end portion as a third projection,
  the fourth traction element at the fourth exit point of tangency onto the proximal end portion as a fourth projection,
  the fifth traction element at the fifth exit point of tangency onto the proximal end portion as a fifth projection, and
  the sixth traction element at the sixth exit point of tangency onto the proximal end portion as a sixth projection,
  and wherein the first, second, third, fourth, fifth and sixth projections are circumferentially arranged in the same order as the circumferential arrangement of the respective through holes on the proximal end portion.

Optionally, the end section may further have an axis line extending from a proximal end to a distal end thereof, wherein the six traction elements all have a diameter of d, and wherein the projections of the traction elements on the proximal end portion are so configured
  that a center of the sixth projection is located within a circular area, which is centered at a point of symmetry of a center of the fifth projection with respect to the axis line and has a radius of 5d,
  that a center of the second projection is located within a circular area, which is centered at a point of symmetry of a center of the third projection with respect to the axis line and has a radius of 5d, and
  that a center of the fourth projection is located within a circular area, which is centered at a point of symmetry of a center of the first projection with respect to the axis line and has a radius of 5d.

Optionally, the surgical instrument may further comprise a rod configured coaxially with the axis line, the rod provided with a through lumen for passage of all the traction elements therethrough, wherein all the traction elements within the rod are configured so that any two of their projections are spaced from each other by a center-to-center distance that is greater than d, that the center of any of their projections is spaced from an inner surface of the rod by a distance greater than 0.6d, and that any of their projections is spaced from the rod by a center-to-center distance greater than 0.5d.

Optionally, the surgical instrument may further comprise a rod configured coaxially with the axis line, the rod provided with a through lumen for passage of the traction elements therethrough,
  wherein if the center of the fifth projection is denoted as A1, a projection of an axis line of the rod as O1, the center of the third projection as B1, the center of the first projection as C1 and an internal diameter of the rod as D, then the third and first projections satisfy:

$$\angle A1O1B1 \in \left[2\arcsin\left(\frac{0.6d}{0.5D - 0.6d}\right), \pi - 4\arcsin\left(\frac{0.6d}{0.5D - 0.6d}\right)\right]; \text{ and}$$

$$\angle A1O1C1 \in \left[4\arcsin\left(\frac{0.6d}{0.5D - 0.6d}\right), \pi - 2\arcsin\left(\frac{0.6d}{0.5D - 0.6d}\right)\right].$$

Optionally, the base may be provided thereon with a first guide base and an opposing second guide base, wherein three of the guide pulleys are disposed on the first guide base and the remaining three guide pulleys on the second guide base.

Optionally, the first, sixth and second guide pulleys may be disposed on the first guide base and the third, fifth and fourth guide pulleys on the second guide base so that the second guide pulley is closer to the base than the sixth guide pulley that is in turn closer to the base than the first guide pulley and that the fourth guide pulley is closer to the base than the fifth guide pulley that is in turn closer to the base than the third guide pulley.

Optionally, the third, first and sixth guide pulleys may be disposed on the first guide base and the fifth, second and fourth guide pulleys on the second guide base so that the sixth guide pulley is closer to the base than the first guide pulley that is in turn closer to the base than the third guide pulley and that the fourth guide pulley is closer to the base than the second guide pulley that is in turn closer to the base than the fifth guide pulley.

Optionally, the end section may further have an axis line extending from a proximal end to a distal end thereof, wherein the base has a first plane of symmetry and a second plane of symmetry perpendicular to the first plane of symmetry, the first plane of symmetry intersecting the second plane of symmetry along a line that is parallel to or collinear with the axis line, wherein the second end drive shaft is symmetrical to the third end drive shaft with respect to the first plane of symmetry, wherein the first end drive shaft is symmetrical to the second end drive shaft with respect to the second plane of symmetry, and wherein the second end drive shaft is farther away from the axis line than the third end drive shaft.

Optionally, the end section may further have an axis line extending from a proximal end to a distal end thereof, wherein the base has a first plane of symmetry and a second plane of symmetry perpendicular to the first plane of symmetry, the first plane of symmetry intersecting the second plane of symmetry along a line that is parallel to or collinear with the axis line, wherein the second end drive shaft is symmetrical to the third end drive shaft with respect to the first plane of symmetry, wherein the first end drive shaft is symmetrical to the third end drive shaft with respect to the second plane of symmetry, and wherein the third end drive shaft is farther away from the axis line than the second end drive shaft.

Optionally, the end section may have at least two degrees of freedom, wherein the wire transmission comprises a fourth transmission module and a fifth transmission module, each of the fourth and fifth transmission modules configured to drive the end section to move in a respective one of the degrees of freedom, the fourth transmission module comprising a fourth end drive shaft, a seventh traction element, an eighth traction element, a seventh guide pulley and an eighth guide pulley, the fifth transmission module comprising a fifth end drive shaft, a ninth traction element, a tenth traction element, a ninth guide pulley and a tenth guide pulley, and wherein the seventh, eighth, ninth and tenth traction elements correspond to the seventh, eighth, ninth and tenth guide pulleys, respectively.

Optionally, the end section may further comprise a snake-like robot arm comprising a plurality of links, which are chained together axially and able to swing in at least two directions, thereby providing at least two degrees of freedom, Wherein the seventh, eighth, ninth and tenth traction elements are passed through the links successively and coupled to a most distal one of the links, and wherein the fourth and fifth transmission modules are configured to drive the snake-like robot arm to swing in two directions.

Optionally, the proximal end portion may be provided with a seventh through hole, an eighth through hole, a ninth through hole and a tenth through hole for constraining extension of the seventh traction element, the eighth traction element, the ninth traction element and the tenth traction element, respectively, wherein the seventh, ninth, eighth and tenth through holes are arranged circumferentially on the proximal end portion.

Optionally, the seventh through hole may be symmetrical to the eighth through hole with respect to a center of the proximal end portion, wherein the ninth through hole is symmetrical to the tenth through hole with respect to the center of the proximal end portion.

Optionally, the seventh guide pulley, the eighth guide pulley, the ninth guide pulley and the tenth guide pulley may have a seventh exit point of tangency, an eighth exit point of tangency, a ninth exit point of tangency and a tenth exit point of tangency, respectively, wherein the seventh traction element is projected at the seventh exit point of tangency onto the proximal end portion as a seventh projection, the eighth traction element is projected at the eighth exit point of tangency onto the proximal end portion as an eighth projection, the ninth traction element is projected at the ninth exit point of tangency onto the proximal end portion as a ninth projection, and the tenth traction element is projected at the tenth exit point of tangency onto the proximal end portion as a tenth projection, and wherein the seventh, eighth, ninth and tenth projections are circumferentially arranged in the same order as the circumferential arrangement of the respective through holes on the proximal end portion.

Optionally, the end section may further have an axis line extending from a proximal end to a distal end thereof, wherein the four traction elements all have a diameter of d, and wherein the projections of the traction elements on the proximal end portion are so configured that a center of the eighth projection is located within a circular area, which is centered at a point of symmetry of a center of the seventh projection with respect to the axis line and has a radius of 5d, and that a center of the tenth projection is located within a circular area, which is centered at a point of symmetry of a center of the ninth projection with respect to the axis line and has a radius of 5d.

Optionally, the surgical instrument may further comprise a rod configured coaxially with the axis line, the rod provided with a through lumen for passage of the traction elements therethrough, wherein all the traction elements within the rod are configured so that any two of their projections are spaced from each other by a center-to-center distance greater than d, that the center of any of their projections is spaced from an inner surface of the rod by a distance greater than 0.6d, and that any of their projections is spaced from the rod by a center-to-center distance greater than 0.5d.

Optionally, the surgical instrument may further comprise a rod configured coaxially with the axis line, the rod provided with a through lumen for passage of the traction elements therethrough, wherein if a projection of an axis line of the rod is denoted as O1, the center of the eighth projection as Q1, the center of the ninth projection as P1 and an internal diameter of the rod as D, then the ninth and eighth projections satisfy:

$$\angle P1O1Q1 \in \left[2acrsin\left(\frac{0.6d}{0.5D-0.6d}\right), \pi - 2acrsin\left(\frac{0.6d}{0.5D-0.6d}\right)\right].$$

Optionally, the base may be provided thereon with a third guide base and an opposing fourth guide base, wherein the seventh and eighth guide pulleys are disposed on the third guide base and the ninth and tenth guide pulleys on the fourth guide base so that the seventh guide pulley is closer to the base than the eighth guide pulley and that the ninth guide pulley is closer to the base than the tenth guide pulley.

In order to overcome at least one of the above-described problems, the present invention also provides a surgical robot comprising a mechanical arm and the surgical instrument as defined above. The surgical instrument is disposed at an end of the mechanical arm, and the mechanical arm is configured to adjust a position and/or orientation of the surgical instrument.

In summary, the present invention provides a surgical robot and a surgical instrument. The surgical instrument includes a wire transmission and an end section. The wire transmission includes a base and n transmission modules each including at least one end drive shaft, two traction elements and two guide pulleys. Each of the guide pulleys comprises a groove for receiving therein a respective one of the traction elements. The groove has a plane of rotation, an entry point of tangency and an exit point of tangency. An angle between the plane of rotation and the traction element defined by the end drive shaft and the entry point of tangency is in the range of 0-0.2°. Projections of all the traction elements at the respective exit points of tangency on the proximal end portion are circumferentially arranged in the same order as the circumferential arrangement of the respective through holes. This design reduces or eliminates frictional resistance between the grooves of the guide pulleys and the traction elements while using fewer guide pulleys in the wire transmission of the surgical instrument. Additionally, the traction elements will not push or rub against one another, resulting in improved transmission efficiency of the wire transmission and an extended service life of the surgical instrument.

BRIEF DESCRIPTION OF THE DRAWINGS

Those of ordinary skill in the art would appreciate that the following drawings are presented merely to enable a better understanding of the present invention rather than to limit the scope thereof in any sense. In the drawings:

FIGS. 26(A) and 26(B) schematically illustrates the cases where $\angle P1O1Q1$ is respectively minimum and maximum in the rod's cross-section according to the fourth embodiment of the present invention; and FIG. 27 schematically illustrates an angle of deflection of a first segment of a first guide pulley from a first traction element according to the first embodiment of the present invention.

Figure 1:
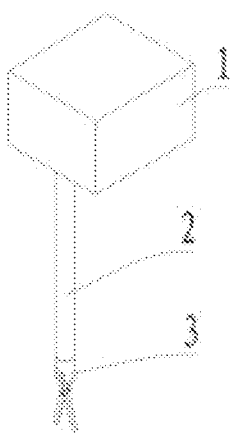
FIG. 1 shows a schematic structural overview of a surgical instrument according to a first embodiment of the present invention.

In these figures, 1 denotes a wire transmission; 11, a base; 12, a first end drive shaft; 13, a second end drive shaft; 14, a third end drive shaft; 15, a guide frame base; 16, a second guide base; 161, a third guide pulley; 162, a third guide pulley rotational axle; 163, a fifth guide pulley; 164, a rotational axle for the fifth guide pulley; 165, a fourth guide pulley; 166, a rotational axle for the fourth guide pulley; 17, a first guide base; 171, a first guide pulley; 172, a rotational axle for the first guide pulley; 173, a sixth guide pulley; 174, a rotational axle for the sixth guide pulley; 175, a second guide pulley; 176, a rotational axle for the second guide pulley; 181, a third guide base; 182, a fourth guide base; 191, a fifth end drive shaft; 192, a sixth end drive shaft; 193, a seventh guide pulley; 194, an eighth guide pulley; 195, a ninth guide pulley; 196, a tenth guide pulley;

2, a rod; 21, a fifth traction element; 22, a third traction element; 23, a first traction element; 24, a sixth traction element; 25, a second traction element; 26, a fourth traction element; 201, a ninth traction element; 202, an eighth traction element; 203, a tenth traction element; 204, a seventh traction element;

3, an end section; 300, a proximal end portion; 21b, a fifth through hole; 22b, a third through hole; 23b, a first through hole; 24b, a sixth through hole; 25b, a second through hole; 26b, a fourth through hole; 201b, a ninth through hole; 202b, an eighth through hole; 203b, a tenth through hole; 204b, a seventh through hole;

301, an effector base; 302, a first openable and closable plate member; 303, a second openable and closable plate member; 304, a first rotational axle; 305, a second rotational axle; 306, a first end guide pulley; 307, a second end guide pulley; 308, a third end guide pulley; 309, a fourth end guide pulley; and 311, a link of a snake-like robot arm.

DETAILED DESCRIPTION

Objects, advantages and features of the present invention will become more apparent from the following more detailed description of particular embodiments made in conjunction with the accompanying drawings. Note that the figures are provided in a very simplified form not necessarily drawn to exact scale for the only purpose of helping to explain the disclosed embodiments in a more convenient and clearer way. In addition, structures shown in the figures are usually part of actual structures. In particular, as the figures tend to have distinct emphases, they are often drawn to different scales.

As used herein and in the appended claims, the singular forms "a", "an" and "the" include plural referents unless the context clearly dictates otherwise. As used herein and in the appended claims, the term "or" is employed in the sense including "and/or", unless the context clearly dictates otherwise. In addition, the term "proximal" is generally used to refer to an end of a surgical instrument that is closer to an operator who is operating the surgical instrument to perform an operation on an object, and the term "distal" is generally used to refer to an end of the surgical instrument that is closer to the object.

The core idea of the present invention is to provide a surgical robot and a surgical instrument. The surgical instrument includes a wire transmission and an end section. The wire transmission comprises a base and n transmission modules each comprising at least one end drive shaft, two traction elements and two guide pulleys. The end section has at least n degrees of freedom and comprises a proximal end portion provided with 2n circumferentially arranged through holes. The end drive shaft is rotatably disposed on the base and is configured to drive the end section to move via the traction elements. In an $i^{th}$ one of the transmission modules, the $j^{th}$ and $(j+1)^{th}$ traction elements are proximally wound on the $i^{th}$ end drive shaft in opposite directions, and are distally guided by the $j^{th}$ and $(j+1)^{th}$ guide pulleys toward $j^{th}$ and $(j+1)^{th}$ ones of the through holes, respectively, and then passed through the $j^{th}$ and $(j+1)^{th}$ through holes, respectively, where i is a natural number in the range from 1 to n, and j=2i−1. Each of the guide pulleys comprises a groove for receiving therein a respective one of the traction elements. The groove has a plane of rotation, an entry point of tangency and an exit point of tangency. The traction element is configured to enter the guide pulley at the entry point of tangency and leave the guide pulley at the exit point of tangency. The guide pulley is configured so that an angle between the plane of rotation and the traction element defined by the end drive shaft and the entry point of tangency is in the range of 0-0.2°. Projections of all the traction elements at the respective exit points of tangency on the proximal end portion are circumferentially arranged in the same order as the circumferential arrangement of the respective through holes.

This design reduces or eliminates frictional resistance between the grooves of the guide pulleys and the traction elements while using fewer guide pulleys in the wire transmission of the surgical instrument. Additionally, the traction elements will not push or rub against one another, resulting in improved transmission efficiency of the wire transmission and an extended service life of the surgical instrument.

The present invention will be described below with reference to the accompanying drawings.

Embodiment 1

Figure 2:
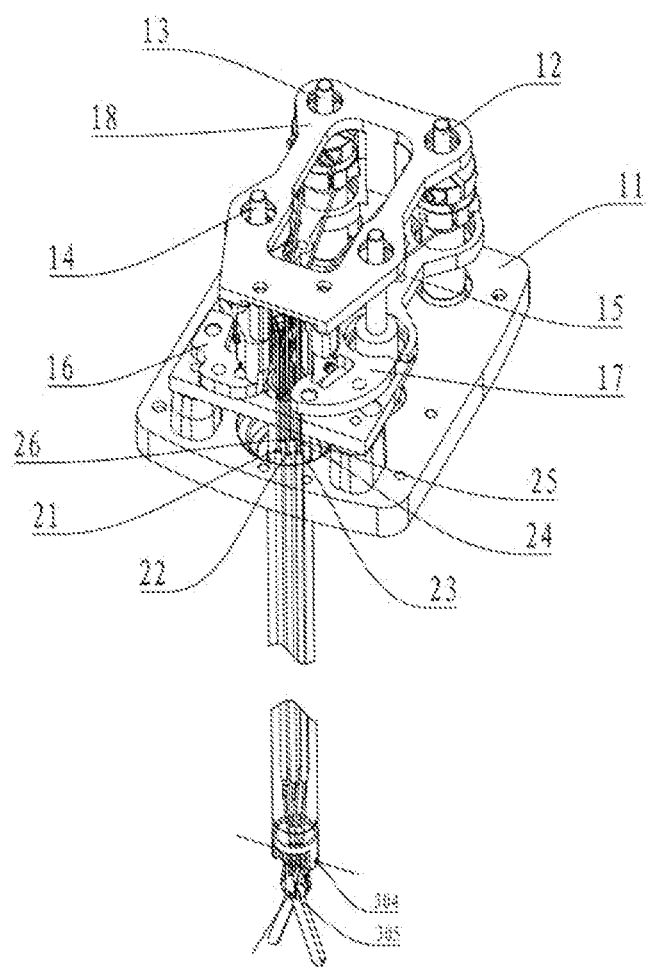
FIG. 2 schematically illustrates internal structural details of the surgical instrument according to the first embodiment of the present invention.
Figure 3:
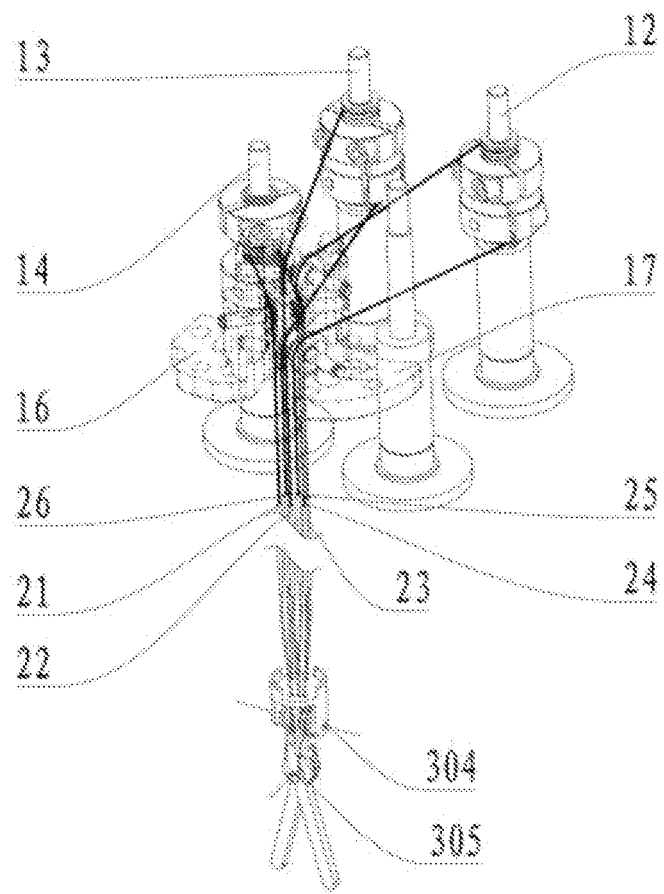
FIG. 3 is a schematic illustration of a wire transmission according to the first embodiment of the present invention.
Figure 4:
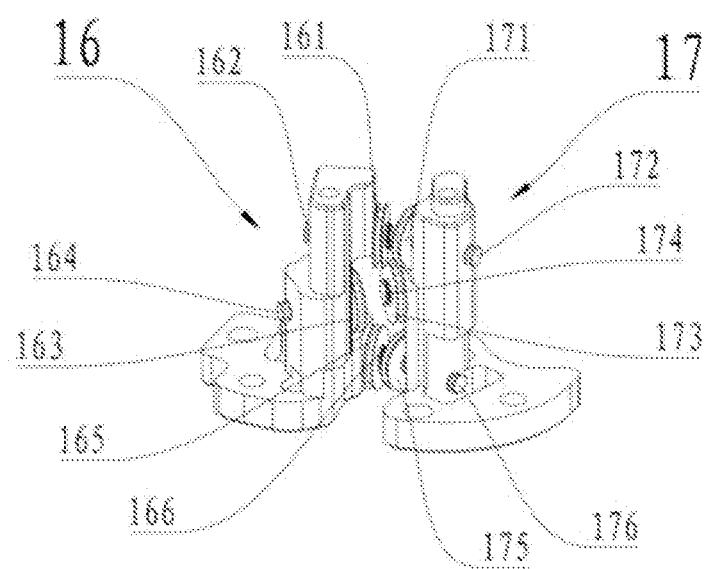
FIG. 4 is a schematic illustration of guide bases according to the first embodiment of the present invention.
Figure 5:
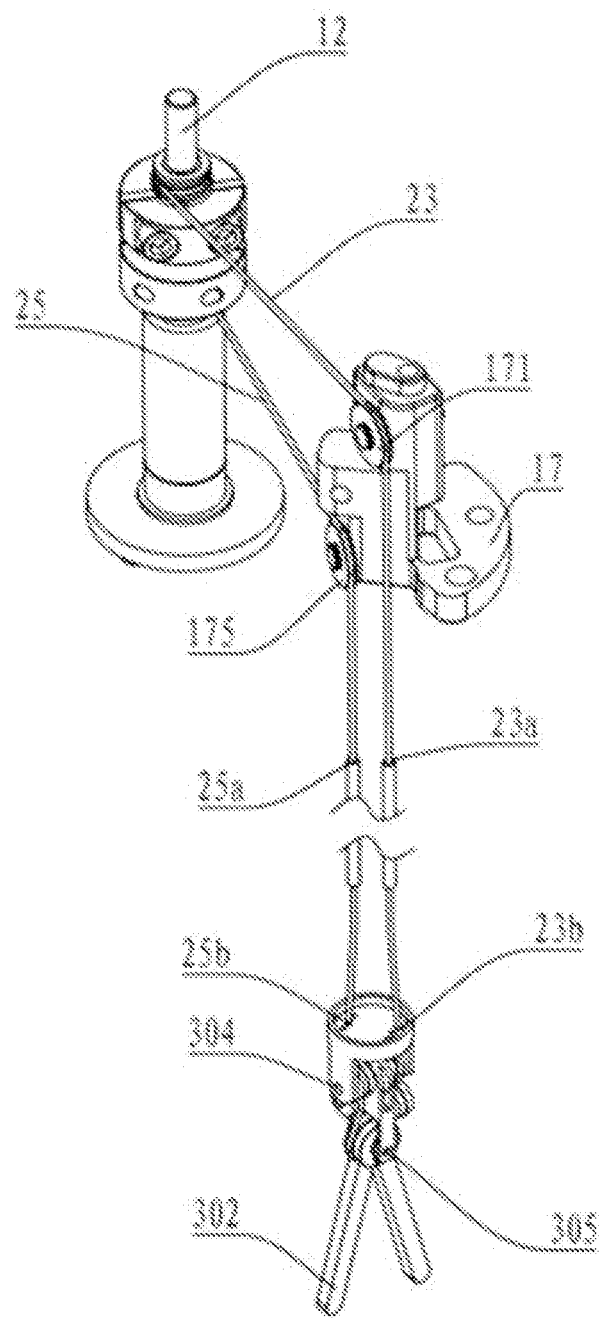
FIG. 5 is a schematic illustration of a first transmission module according to the first embodiment of the present invention.
Figure 6:
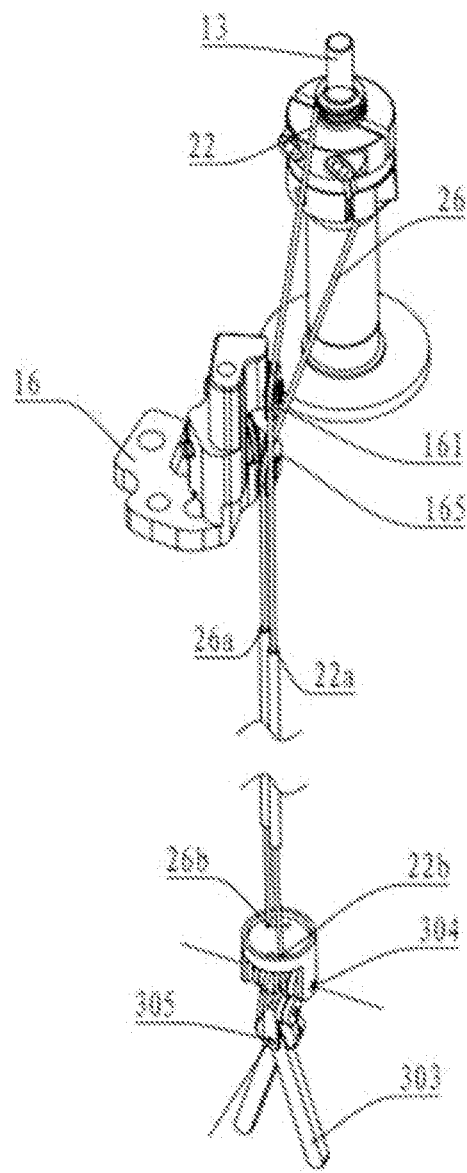
FIG. 6 is a schematic illustration of a second transmission module according to the first embodiment of the present invention.
Figure 7:
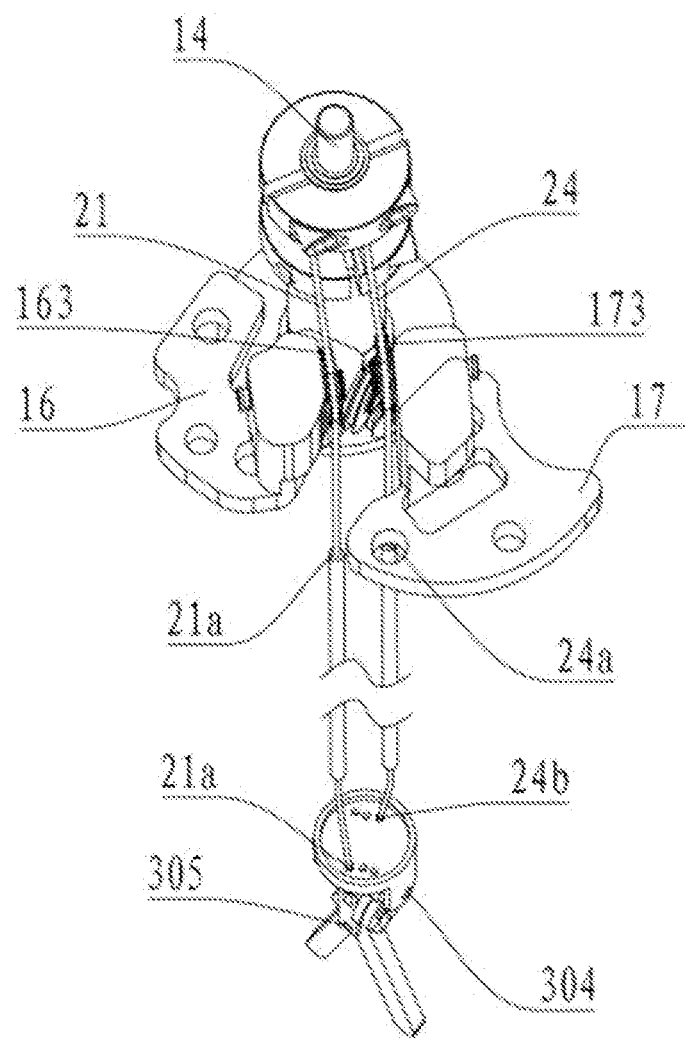
FIG. 7 is a schematic illustration of a third transmission module according to the first embodiment of the present invention.
Figure 8:
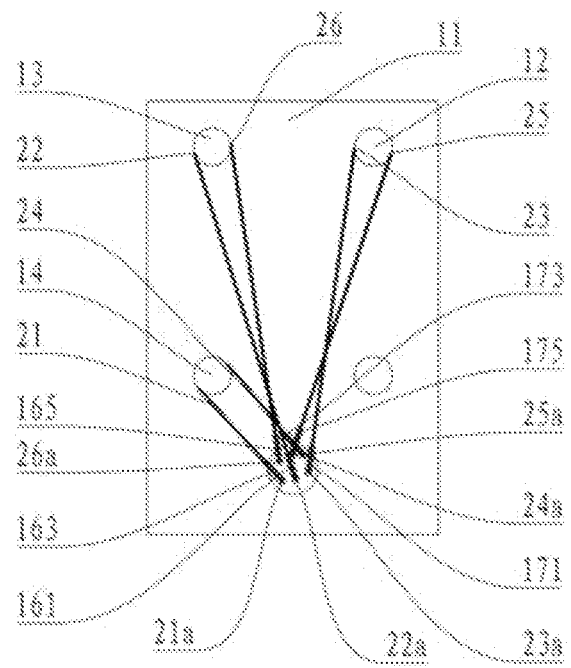
FIG. 8 schematically illustrates a transmission plane of the wire transmission according to the first embodiment of the present invention.
Figure 9:
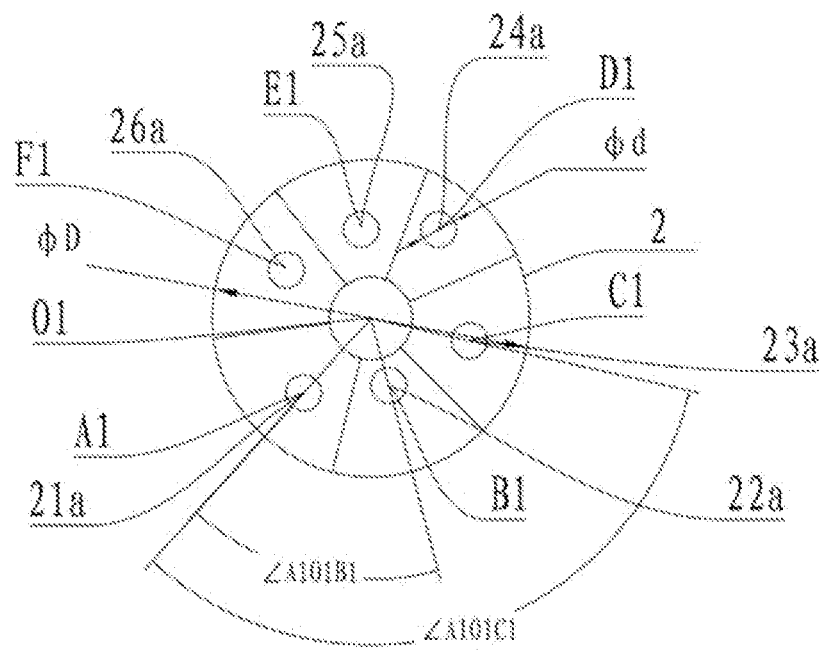
FIG. 9 is a schematic cross-sectional view of a rod at a proximal end thereof according to the first embodiment of the present invention.
Figure 10A:
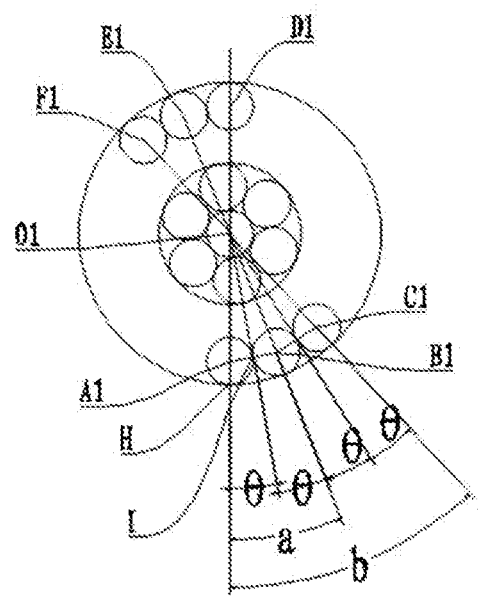
FIGS. 10(A) and 10(B) schematically illustrates the cases where $\angle A1O1B1$ and $\angle A1O1C1$ are respectively minimum and maximum in the rod's cross-section according to the first embodiment of the present invention.
Figure 10B:
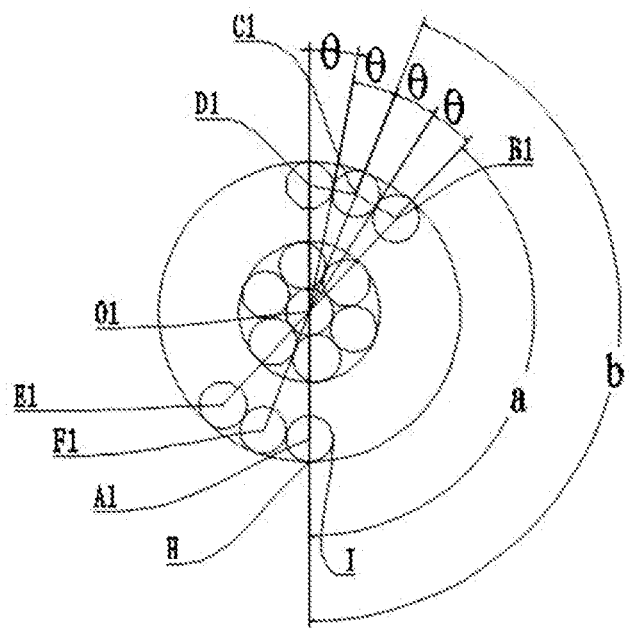
Figure 11A:
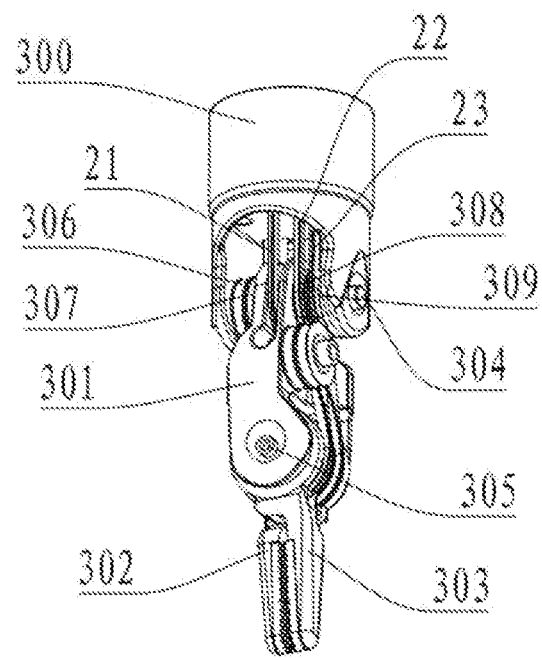
FIGS. 11(A) and 11(B) are schematic illustrations of an end section according to the first embodiment of the present invention.
Figure 11B:
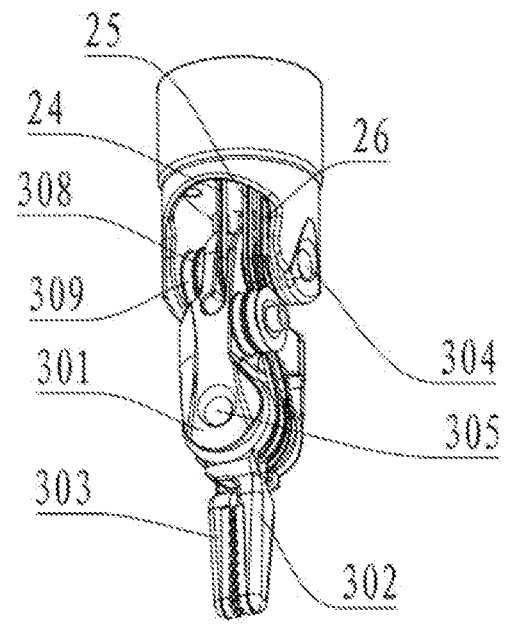
Figure 12:
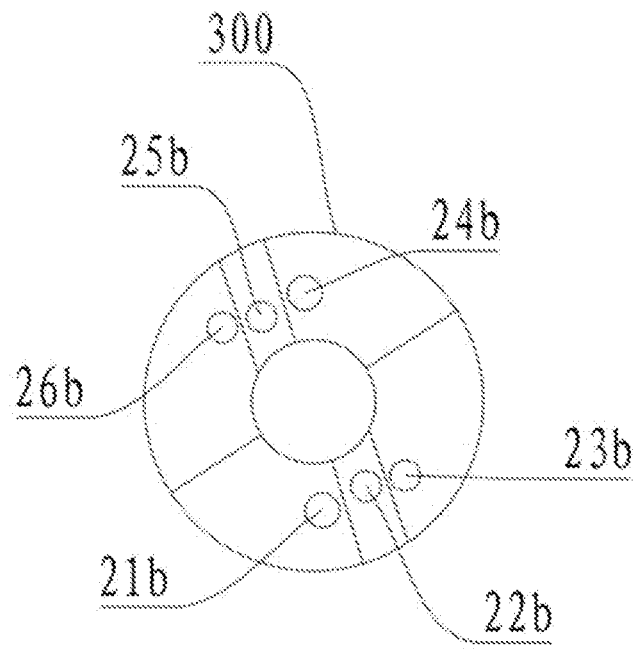
FIG. 12 is a schematic illustration of a proximal end portion of the end section according to the first embodiment of the present invention.
Figure 13:
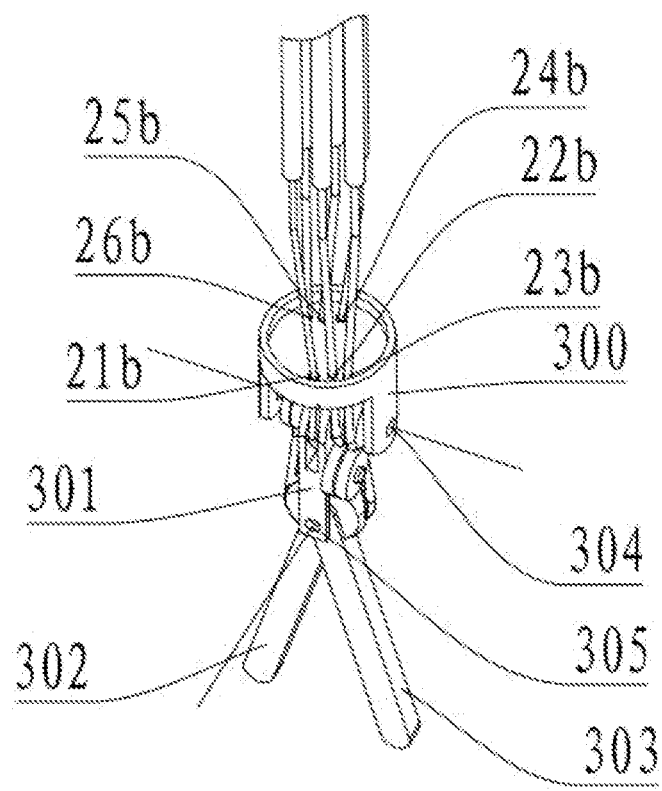
FIG. 13 schematically illustrates how the wire transmission is coupled to the end section according to the first embodiment of the present invention.

Reference is now made to FIGS. 1 to 9, FIGS. 10(A) and 10(B), FIGS. 11(A) and 11(B), 12 to 13 and 27. FIG. 1 shows a schematic structural overview of a surgical instrument according to a first embodiment of the present invention. FIG. 2 schematically illustrates internal structural details of the surgical instrument according to the first embodiment of the present invention. FIG. 3 is a schematic illustration of a wire transmission according to the first embodiment of the present invention. FIG. 4 is a schematic illustration of guide bases according to the first embodiment of the present invention. FIG. 5 is a schematic illustration of a first transmission module according to the first embodiment of the present invention. FIG. 6 is a schematic illustration of a second transmission module according to the first embodiment of the present invention. FIG. 7 is a schematic illustration of a third transmission module according to the first embodiment of the present invention. FIG. 8 schematically illustrates a transmission plane of the wire transmission according to the first embodiment of the present invention. FIG. 9 is a schematic cross-sectional view of a rod at a proximal end thereof according to the first embodiment of the present invention. FIGS. 10(A) and 10(B) schematically illustrates the cases where ∠A1O1B1 and ∠A1O1C1 are respectively minimum and maximum in the rod's cross-section according to the first embodiment of the present invention. FIGS. 11(A) and 11(B) are schematic illustrations of an end section according to the first embodiment of the present invention. FIG. 12 is a schematic illustration of a proximal end portion of the end section according to the first embodiment of the present invention. FIG. 13 schematically illustrates how the wire transmission is coupled to the end section according to the first embodiment of the present invention. FIG. 27 schematically illustrates an angle of deflection of a first segment of a first guide pulley from a first traction element according to the first embodiment of the present invention.

As shown in FIGS. 1 and 2, a surgical instrument according to the first embodiment of the present invention includes a wire transmission 1 and an end section 3. Traction elements in the wire transmission are connected to the end section 3, and the wire transmission is configured to drive the end section 3. Preferably, the surgical instrument further includes a rod 2 which connects the wire transmission 1 to the end section 3.

Referring to FIGS. 11(A) and 11(B), the end section 3 includes a proximal end portion 300 and an end effector. Preferably, between the proximal end portion 300 and the end effector, the end section 3 further includes one or more joints for enabling pitch or yaw motions of the end effector. In one embodiment, the end section has three degrees of freedom enabled by six traction elements. Referring to FIG. 12, in connection with FIG. 13, the proximal end portion 300 is provided with 6 circumferentially spaced through holes for passage of the respective traction elements therethrough. The 6 through holes are respectively a first through hole 23b, a second through hole 25b, a third through hole 22b, a fourth through hole 26b, a fifth through hole 21b and a sixth through hole 24b. Here, the relative positioning of the through holes depends on how the joints in the end section 3 are arranged. Those skilled in the art may design the arrangement of the joints and the corresponding relative positioning of the through holes as practically needed.

FIGS. 11(A) and 11(B) are schematic opposite (left and right) side views of the end section 3 according to the first embodiment. The end effector is rotatably coupled to the proximal end portion 300. The end effector includes an effector base 301, a first openable and closable plate member 302 and a second openable and closable plate member 303. The first and second openable and closable plate members 302 and 303 are rotatably coupled to the effector base 301, thereby providing at least two degrees of freedom. The effector base 301 is rotatably coupled to the proximal end portion 300, thereby providing at least one degree of freedom. In one exemplary embodiment, the effector base 301 is coupled to a distal end of the proximal end portion 300 so as to be rotatable about a first rotational axle 304, and both the first and second openable and closable plate members 302 and 303 are coupled to the effector base 301 so as to be rotatable about a second rotational axle 305. The rotatability of the effector base 301 relative to the proximal end portion 300 provides a degree of swing freedom, and the rotatability of the two openable and closable plate members relative to the effector base 301 provides two degrees of opening and closing freedom. Therefore, the end section has three degrees of freedom. Preferably, every two of an axis line of the end section 3, the first rotational axle 304 and the second rotational axle 305 are perpendicular to each other.

The wire transmission 1 according to the first embodiment of the present invention is described below with reference to FIG. 3, in connection with FIGS. 2 and 4. The wire transmission 1 includes a base 11 and three transmission modules. Each of the transmission modules includes at least one end drive shaft, two traction elements and two guide pulleys. All the end drive shafts are rotatably disposed on the base 11, and the traction elements are configured to drive the end section 3 to move. The three transmission modules are respectively a first transmission module, a second transmission module and a third transmission module. The first transmission module includes at least a first end drive shaft 12, a first traction element 23, a second traction element 25, a first guide pulley 171 and a second guide pulley 175. The second transmission module includes at least a second end drive shaft 13, a third traction element 22, a fourth traction element 26, a third guide pulley 161 and a fourth guide pulley 165. The third transmission module includes at least a third end drive shaft 14, a fifth traction element 21, a sixth traction element 24, a fifth guide pulley 163 and a sixth guide pulley 173. Preferably, the base 11 has a first plane of symmetry and a second plane of symmetry, which are perpendicular to each other. Additionally, the first and section planes of symmetry intersect along a line that is parallel to or collinear with the axis line of the end section 3. The second end drive shaft 13 and the third end drive shaft 14 are arranged in symmetry with respect to the first plane of symmetry, and the second end drive shaft 13 is located farther away from the axis line of the end section 3 than the third end drive shaft 14. The first end drive shaft 12 and the second end drive shaft 13 are arranged in symmetry with respect to the second plane of symmetry.

Referring to FIGS. 5 to 7, in connection with FIGS. 11(A) and 11(B), 12 and 13, the three transmission modules in the wire transmission 1 are configured to drive movement of the end section 3. Specifically, the first transmission module is configured to cause rotation of the first openable and closable plate member 302, the second transmission module is configured to cause rotation of the second openable and closable plate member 303, and the third transmission module is configured to cause the end effector to rotate relative to the proximal end portion 300. More specifically, the fifth and sixth traction elements 21 and 24 in the third transmission module extend on opposing sides of the first rotational axle 304 and fixedly coupled to the effector base 301 so as to be able to cause the effector base 301 to rotate about the first rotational axle 304. In addition, four end guide pulleys, i.e., a first end guide pulley 306, a second end guide pulley 307, a third end guide pulley 308 and a fourth end guide pulley 309, are disposed over and rotatably coupled to the first rotational axle 304. The first end guide pulley 306 and the fourth end guide pulley 309 are arranged in symmetry with respect to the axis line of the end section 3, and the second end guide pulley 307 and the third end guide pulley 308 are also arranged in symmetry with respect to the axis line of the end section 3. The second end guide pulley 307 and the third end guide pulley 308 are located closer to the axis line of the end section 3 than the first end guide pulley 306 and the fourth end guide pulley 309, respectively. The first end guide pulley 306, the second end guide pulley 307, the third end guide pulley 308 and the fourth end guide pulley 309 are provided to guide and alter the extension directions of the fourth traction element 26, the second traction element 25, the third traction element 22 and the first traction element 23, respectively. The first traction element 23 and the second traction element 25 are both fixedly coupled to the first openable and closable plate member 302 so as to be able to cause the first openable and closable plate member 302 to pivot to an open or closed position, thus providing one degree of opening and closing freedom. The third traction element 22 and the fourth traction element 26 are both fixedly coupled to the second openable and closable plate member 303 so as to be able to cause the second openable and closable plate member 303 to pivot to an open or closed position, thus providing another degree of opening and closing freedom. Preferably, in order to synchronize length variation of the third and fourth traction elements 22 and 26 for driving movement of the second openable and closable plate member 303 with that of the first and second traction elements 23 and 25 for driving movement of the first openable and closable plate member 302, the second end guide pulley 307 and the third end guide pulley 308 are equal in diameter, and the first end guide pulley 306 and the fourth end guide pulley 309 are equal in diameter.

Referring to FIGS. 12 and 13, the six through holes are provided around a center of the proximal end portion 300 in order to constrain the directions of distal extension of the respective six traction elements in the three transmission modules. Each of the traction elements is coupled proximally to a respective one of the end drive shafts and distally to the end section 3 after passing through a respective one of the through holes. In this embodiment, the first traction element 23 is inserted through the first through hole 23b, the second traction element 25 through the second through hole 25b, the third traction element 22 through the third through hole 22b, the fourth traction element 26 through the fourth through hole 26b, the fifth traction element 21 through the fifth through hole 21b, and the sixth traction element 24 through the sixth through hole 24b. Additionally, the through holes are arranged around the center of the proximal end portion 300 counterclockwise in the order: the fifth through hole 21b, the third through hole 22b, the first through hole 23b, the sixth through hole 24b, the second through hole 25b and the fourth through hole 26b. The fifth and sixth through holes 21b and 24b for passage of the fifth and sixth traction elements 21 and 24 therethrough are arranged in symmetry with respect to the center of the proximal end portion 300. Preferably, a line connecting the fifth through hole 21b and the sixth through hole 24b is perpendicular to an axis line of the first rotational axle 304, in order to allow easy fixed coupling of the fifth traction element 21 and the sixth traction element 24 to the effector base 301, respectively, after they are passed through the fifth through hole 21b and the sixth through hole 24b, respectively, to enable the effector base 301 to rotate about the first rotational axle 304. The third and second through holes 22b and 25b are arranged in symmetry with respect to the center of the proximal end portion 300, and the first and fourth through holes 23b and 26b are arranged in symmetry with respect to the center of the proximal end portion 300. The distance from the third through hole 22b to the center of the proximal end portion 300 is less than the distance from the first through hole 23b to the center of the proximal end portion 300. The third through hole 22b and the second through hole 25b are provided to allow passage of the third traction element 22 and the second traction element 25 therethrough. The first through hole 23b and the fourth through hole 26b are provided to allow passage of the first traction element 23 and the fourth traction element 26 therethrough. In other words, the third and fourth through holes 22b and 26b are for accommodating the traction elements for driving movement in one degree of opening and closing freedom, and the first and second through hole 23b and 25b are for accommodating the traction elements for driving movement in the other degree of opening and closing freedom. In addition, arranging the third traction element 22 and the second traction element 25 closer to the center of the proximal end portion 300 than the first traction element 23 and the fourth traction element 26, respectively, make movement of the four traction elements smoother. A line connecting the third through hole 22b and the first through hole 23b may be either parallel to the axis line of the first rotational axle 304 or not. In an alternative embodiment, the through holes are arranged around the center of the proximal end portion 300 clockwise in the order: the fifth through hole 21b, the third through hole 22b, the first through hole 23b, the sixth through hole 24b, the second through hole 25b and the fourth through hole 26b.

In this embodiment, each of the traction elements is trained on a respective one of the guide pulleys and then thus runs in a different direction distally. Each of the guide pulleys comprises a groove for receiving a respective one of the traction elements. The groove has a plane of rotation Gr (as shown in FIG. 27), an entry point of tangency and an exit point of tangency. The traction element enters the guide pulley at the entry point of tangency and leaves the guide pulley at the exit point of tangency. The plane of rotation Gr is perpendicular to an axis of rotation of the guide pulley. Referring to FIG. 5, taking the first guide pulley 171 as an example, it has a first entry point of tangency and a first exit point of tangency. The first traction element 23 enters the first guide pulley 171 at the first entry point of tangency and leaves the first guide pulley 171 at the first exit point of tangency. In this way, the first traction element 23 is guided by the first guide pulley 171 to run in a different direction. Further, referring to FIG. 27, the first guide pulley 171 comprises a groove for receiving the first traction element 23. The groove has a plane of rotation Gr that is perpendicular to a rotational axle 172 of the first guide pulley 171. The first end drive shaft 12 is coupled to the first traction element 23 at a first junction. For ease of description, a segment of the first traction element 23 between the first junction and the first entry point of tangency of the first guide pulley 171 is referred to as a first segment of the first traction element 23. The first guide pulley 171 is configured so that, with respect to the plane of rotation Gr of the first guide pulley 171, the first segment of the first traction element 23 extends at an angle $\alpha$ of 0-0.2°, preferably 0-0.1°, more preferably 0°. In other words, the extension direction of the first traction element 23 is substantially aligned with the plane of rotation Gr of the first guide pulley 171. In this way, the first traction element 23 will not produce a lateral force component on a side wall of the groove due to an angle of deflection, thus resulting in improved transmission efficiency and a prolonged service life of the wire transmission 1. Moreover, as the lateral force component biases the first traction element 23 along an axial direction of the first guide pulley 171 and may cause the first traction element 23 to wobble or fall off from the pulley, eliminating the angle of deflection can avoid/mitigate these adverse impacts. The remaining guide pulleys and the respective traction elements are structured and configured in the same manner as the first guide pulley 171, and a detailed description thereof is deemed unnecessary and omitted. Further, the first segment of the first traction element 23 is inclined at an angle of 0-10° from the base 11. Likewise, a segment of each remaining traction element between its junction with the respective end drive shaft and the entry point of tangency of the respective guide pulley is also referred to as a first segment. Moreover, the first segment of each remaining traction element is configured to form an angle of 0-0.2°, preferably 0-0.1°, more preferably 0°, with the plane of rotation Gr of the respective guide pulley, and an angle of 0-10° with the base 11. Furthermore, in order to avoid the traction elements from abrading and rubbing against one another, the first segments of any two of them may be parallel to each other or extend in different planes.

As the positions of the exit points of tangency of the guide pulleys determine the positions of projections of the respective traction elements at their exit points of tangency on the proximal end portion 300, the guide pulleys are so configured that the positions of the projections of the respective traction elements at their exit points of tangency on the proximal end portion 300 are arranged circumferentially in line with the circumferential arrangement of the respective through holes. Specifically, the circumferential arrangement of the positions of the projections of the respective traction elements at their exit points of tangency on the proximal end portion 300 may be the same as the circumferential arrangement of the through holes in the proximal end portion 300. As shown in FIGS. 8 and 9, in connection with FIG. 3, the through holes are arranged counterclockwise around the center of the proximal end portion 300 in the order: the fifth through hole 21b, the third through hole 22b, the first through hole 23*b*, the sixth through hole 24*b*, the second through hole 25*b* and the fourth through hole 26*b*. The exit points of tangency of the first guide pulley 171, the second guide pulley 175, the third guide pulley 161, the fourth guide pulley 165, the fifth guide pulley 163 and the sixth guide pulley 173 are respectively a first exit point of tangency, a second exit point of tangency, a third exit point of tangency, a fourth exit point of tangency, a fifth exit point of tangency and a sixth exit point of tangency. The first 171 to sixth 173 guide pulleys are configured so that the first projection of the first traction element 23 at the first exit point of tangency on the proximal end portion 300, the second projection of the second traction element 25 at the second exit point of tangency on the proximal end portion 300, the third projection of the third traction element 22 at the third exit point of tangency on the proximal end portion 300, the fourth projection of the fourth traction element 26 at the fourth exit point of tangency on the proximal end portion 300, the fifth projection of the fifth traction element 21 at the fifth exit point of tangency on the proximal end portion 300 and the sixth projection of the sixth traction element 24 at the sixth exit point of tangency on the proximal end portion 300 are circumferentially arranged in the same manner as the through holes. This arrangement allows the segments of the traction elements between the respective exit points of tangency and the respective through holes to be neatly arranged in the same order, thus preventing the traction elements from pushing and rubbing against one another and resulting in improved transmission efficiency and an extended service life of the wire transmission 1.

Preferably, the guide pulleys are also configured so that each of the segments of the traction elements between the respective exit points of tangency and the respective through holes forms an angle of 0-5° with the axis line of the end section 3. Taking the first guide pulley 171 as an example, the segment of the first traction element 23 between the first exit point of tangency of the first guide pulley 171 where it leaves the first guide pulley 171 and the first through hole 23*b* through which it is inserted is referred to as a second segment 23*a*. In practice, the second segment 23*a* of the first traction element 23 may form an angle of 0-5° with the axis line of the end section 3, meaning that the second segment 23*a* of the first traction element 23 extends substantially along the axis line of the end section 3. Likewise, the segment of each remaining traction element between the exit point of tangency of the respective guide pulley and the respective through hole is referred to as a second segment of the specific traction element, and the second segments of all the remaining traction elements (i.e., the second segment 25*a* of the second traction element 25, the second segment 22*a* of the third traction element 22, the second segment 26*a* of the fourth traction element 26, the second segment 21*a* of the fifth traction element 21 and the second segment 24*a* of the sixth traction element 24) may form an angle that is not greater than 5° with the axis line of the end section 3. In other words, the extension directions of the second segments of all the traction elements are allowed to be inclined away from the axis line of the end section 3 at an angle that is not greater than 5°. In general terms, the positioning of the traction elements coupled to the end section 3 at the distal end of the surgical instrument is somewhat different from that at the proximal end of the surgical instrument. That is, not all the extension directions of the second segments of the traction elements are parallel to the axis line of the end section 3, and one or more of them may be inclined away at an angle. Through limiting this angle within 5°, frictional resistance generated due to deflection between the traction elements and the respective guide pulleys will be tolerable. In this way, as the second segments of all the traction elements extend along the axis line of the end section 3 while being inclined away therefrom at an angle of less than 5°, the traction elements can be prevented from pushing and rubbing against one another. Additionally, the rod 2 is arranged coaxially with the axis line of the end section 3 and is provided with a through lumen for passage of the traction elements therethrough. Specifically, the second segment of each traction element may be mostly housed within the rod 2, only with a small portion extending out of the rod 2 and being coupled to the respective guide pulley. This arrangement can prevent the traction elements from coming into contact with and scraping the rod 2. The guide pulleys are further configured so that the second segments of the traction elements form angles of 0-1.5° with the planes of rotation Gr of the respective guide pulleys. For example, the second segment 23*a* of the first traction element 23 extends from the first exit point of tangency of the first guide pulley 171 to the first through hole 23*b* forms an angle of 0-1.5° with the plane of rotation Gr of the first guide pulley. All the remaining guide pulleys of the respective traction elements are all configured in the same manner.

With continued reference to FIGS. 8 and 9, the guide pulleys are so configured that the second sections of the six traction elements are circumferentially arranged around an axis line of the surgical instrument in the order: the fifth traction element 21, the third traction element 22, the first traction element 23, the sixth traction element 24, the second traction element 25 and the fourth traction element 26, both upstream and downstream of the rod 2. The counterclockwise circumferential arrangement of the six traction elements around the axis line of the surgical instrument will be described below with reference to the projections of the six traction elements at the exit points of tangency shown in FIG. 9 as an example. Here, an internal diameter of the rod 2 is further taken into account for the arrangement of the traction elements. The axis line of the rod 2 is configured to be collinear with the axis line of the end section 3. Assuming that the six traction elements and hence their projections each have a diameter d and that the internal diameter of the rod 2 is D, with the fifth projection of the fifth traction element 21 being taken as a reference, a center of the sixth projection of the sixth traction element 26 is located within a circular area, which is centered at a point of symmetry of a center of the fifth projection of the fifth traction element 21 with respect to the axis line of the end section 3 and has a radius of 5d. Additionally, a center of the second projection of the second traction element 25 is located within a circular area, which is centered at a point of symmetry of a center of the third projection of the third traction element 22 with respect to the axis line of the end section 3 and has a radius of 5d, and a center of the fourth projection of the fourth traction element 26 is located within a circular area, which is centered at a point of symmetry of a center of the first projection of the first traction element 23 with respect to the axis line of the end section 3 and has a radius of 5d. Moreover, the centers of the projections of every two of the six traction elements are spaced from each other by a distance greater than d in order to prevent them from coming into contact and rubbing against each other. Further, in order to prevent any of the traction elements coming into contact and scraping an inner surface of the rod 2, the center of its projection is spaced from the inner surface of the rod 2 by a distance greater than 0.6d. Here, 0.6d is chosen because it provides more margin over 0.5d, the distance from the center of the projection of any of the traction elements to the inner surface of the rod 2 upon the traction element coming into contact with the inner surface, which can accommodate jittering or wobbling of the traction elements that may occur sometimes, thus avoiding them from coming into contact and scraping the inner surface. Furthermore, the center of any projection is spaced from a center line of the rod 2 by a distance greater than 0.5d. This can prevent traction elements from pushing and rubbing against one another.

More preferably, if the center of the fifth projection of the fifth traction element 21 is denoted as A1, a projection of the axis line of the end section 3 as O1, the center of the third projection of the third traction element 22 as B1, the center of the first projection of the first traction element 23 as C1, the center of the sixth projection of the sixth traction element 24 as D1, the center of the second projection of the second traction element 25 as E1, the center of the fourth projection of the fourth traction element 26 as F1 and the internal diameter of the rod 2 as D, then the third projection of the third traction element 22 and the first projection of the first traction element 23 satisfy:

$$\angle A1O1B1 \in \left[2\arcsin\left(\frac{0.6d}{0.5D-0.6d}\right), \pi - 4\arcsin\left(\frac{0.6d}{0.5D-0.6d}\right)\right]; \text{ and}$$

$$\angle A1O1C1 \in \left[4\arcsin\left(\frac{0.6d}{0.5D-0.6d}\right), \pi - 2\arcsin\left(\frac{0.6d}{0.5D-0.6d}\right)\right].$$

Reference is now made to FIG. 10(A), which shows the case in which ∠A1O1B1 and ∠A1O1C1 are both minimum, and to FIG. 10(B), which shows the case in which ∠A1O1B1 and ∠A1O1C1 are both maximum. In these figures, H denotes the farthest point of the fifth projection of the fifth traction element 21 from the projection O1 of the axis line of the end section 3, and I represents a point where the fifth projection of the fifth traction element 21 comes into contact with the third projection of the third traction element 22. As shown in FIG. 10(A), when a=∠A1O1B1 is minimum, the fifth projection of the fifth traction element 21 is adjacent to the third projection of the third traction element 22. When b=∠A1O1C1 is minimum, the third projection of the third traction element 22 is adjacent to the first projection of the first traction element 23. As shown in FIG. 10(B), when a=∠A1O1B1 is maximum, the sixth projection of the sixth traction element 24 is symmetrical to the fifth projection of the fifth traction element 21 with respect to the center O1 of the rod 2, while the first projection of the first traction element 23 is adjacent to the sixth projection of the sixth traction element 24 and the third projection of the third traction element 22 is adjacent to the first projection of the first traction element 23. Considering any two of the traction elements will abrade against each other when they come into direct contact, a minimum allowable distance between their projections may be set to 1.2d. So, we obtain:

sin θ=1.2*A1I/(O1H−1.2*A1H);

a=∠A1O1B1=2θ; and

A1I=A1H*0.5d,O1H=0.5D, for the case where a=∠A1O1B1 and b=∠A1O1C1 are minimum, as shown in FIG. 10(A).
Therefore, $$a = \angle A1O1B1 = 2\arcsin\left(\frac{0.6d}{0.5D-0.6d}\right),$$

when a=∠A1O1B1 is minimum.
Likewise, $$b = \angle A1O1C1 = 4\arcsin\left(\frac{0.6d}{0.5D-0.6d}\right),$$

when b=∠A1O1C1 is minimum.

For the case where a=∠A1O1B1 and b=∠A1O1C1 are maximum, as shown in FIG. 10(B), we can easily obtain:

$$a = \angle A1O1B1 = \pi - 4\arcsin\left(\frac{0.6d}{0.5D-0.6d}\right)$$

when a=∠A1O1B1 is maximum, and $$b = \angle A1O1C1 = \pi - 2\arcsin\left(\frac{0.6d}{0.5D-0.6d}\right)$$

when b=∠A1O1C1 is maximum.

For the above expressions, D should be large enough to allow the traction elements to be housed within the lumen of the rod 2. With this arrangement, the six traction elements will not come into contact with one another or with the inner surface of the rod 2. As a result, they will encounter less frictional resistance when used to tract the end section 3.

Further, in each transmission module, the two traction elements are configured to be driven by the respective end drive shaft to move by the same amount in opposite directions. For example, proximal end portions of the two traction elements may be wound on the end drive shaft in opposite directions. With this configuration, when the end drive shaft is turned, one of the traction elements will be shortened, and the other will be extended, thus causing a component coupled to the two traction element to rotate.

Referring to FIG. 5, taking the first transmission module as an example, the first traction element 23 and the second traction element 25 are configured so that when the first end drive shaft 12 is turned, the first traction element 23 and the second traction element 25 moves in opposite directions and change in length by the same amount. The first traction element 23 and the second traction element 25 may be wounded on the first end drive shaft 12 in opposite directions and coupled thereto. Specifically, the first traction element 23 may be proximally wound on the first end drive shaft 12 along a forward direction and distally coupled to the end section 3 through the first guide pulley 171 and the first through hole 23b so as to be able to drive the end section 3 to move (in this embodiment, it is fixedly coupled to the first openable and closable plate member 302 in order to drive it to move toward an open or closed configuration). Moreover, the second traction element 25 may be proximally wound on the first end drive shaft 12 along a reverse direction and distally coupled to the end section 3 through the second guide pulley 175 and the second through hole 25b so as to be able to drive the end section 3 to move (in this embodiment, it is fixedly coupled to the first openable and closable plate member 302 in order to drive it to move toward an open or closed configuration). In this way, when the first end drive shaft 12 is turned, the first traction element 23 may be driven to spiral around an axis line of the first end drive shaft 12 in the forward direction (e.g., clockwise) to be further wound on the first end drive shaft 12. At the same time, the second traction element 25 may be driven to spiral around the axis line of the first end drive shaft 12 in the reverse direction (e.g., counterclockwise) to be somewhat unwound from the first end drive shaft 12. As such, the first traction element 23 and the second traction element 25 are enabled to move in opposite directions and change in length by the same amount. Here, it should be noted that the forward and reverse directions in which the traction elements spiral around the axis line of the end drive shaft only refer to two opposite turning directions, and the forward and reverse directions are not limited to being clockwise and counterclockwise, respectively.

Similarly, the third traction element 22 and the fourth traction element 26 are proximally wound on the second end drive shaft 13 in opposite directions and distally coupled to the end section 3 via the third guide pulley 161 and the fourth guide pulley 165, respectively, and the third through hole 23b and the fourth through hole 24b, respectively (in this embodiment, the third traction element 22 and the fourth traction element 26 are fixedly coupled to the second openable and closable plate member 303 distally in order to drive it to move toward an open or closed configuration). The fifth traction element 21 and the sixth traction element 24 are proximally wound on the third end drive shaft 14 in opposite directions and distally coupled to the end section 3 via the fifth guide pulley 163 and the sixth guide pulley 173, respectively, and the fifth through hole 25b and the sixth through hole 26b, respectively (in this embodiment, the fifth traction element 21 and the sixth traction element 24 are fixedly coupled to the effector base 301 distally in order to control it to rotate about the first rotational axle 304).

The wire transmission 1 further includes at least two guide bases. For example, it may include a first guide base 17 and a second guide base 16. Preferably, the guide bases are located closer to the rod 2 than the end drive shafts. Preferably, the first guide base 17 and the second guide base 16 are symmetrical to each other with respect to the second plane of symmetry. The guide pulleys are rotatably or fixedly arranged on the guide bases. Referring to FIG. 4, the second guide base 16, the second end drive shaft 13 and the third end drive shaft 14 may be disposed on one side of the second plane of symmetry, with the first guide base 17 and the first end drive shaft 12 being disposed on the other side of the second plane of symmetry. Among the six guide pulleys (i.e., the first guide pulley 171, the second guide pulley 175, the third guide pulley 161, the fourth guide pulley 165, the fifth guide pulley 163 and the sixth guide pulley 173), three are provided on the first guide base 17 and the other three on the second guide base 16. On each of the guide bases, the three guide pulleys are disposed at different distances from the base 11. For example, the first guide pulley 171, the sixth guide pulley 173 and the second guide pulley 175 may be arranged on the first guide base 17, and the third guide pulley 161, the fifth guide pulley 163 and the fourth guide pulley 165 may be provided on the second guide base 16. Moreover, the second guide pulley 175 may be closer to the base 11 than the sixth guide pulley 173 that is in turn closer to the base 11 than the first guide pulley 171, and the fourth guide pulley 165 may be closer to the base 11 than the fifth guide pulley 163 that is in turn closer to the base 11 than the third guide pulley 161. With this arrangement, the three guide pulleys in each guide pulley set stagger the respective traction elements at different heights, avoiding them from abrading against one another. Through providing two or more guide bases, arranging too many guide pulleys vertically one above another over a single location of the base 11 is avoided, allowing the wire transmission to be less bulky. Optionally, each guide base may include three guide pulley mounts provided with rotational axles for the respective guide pulleys (in this embodiment, a rotational axle 172 for the first guide pulley, a rotational axle 176 for the second guide pulley, a rotational axle 162 for the third guide pulley, a rotational axle 166 for the fourth guide pulley, a rotational axle 164 for the fifth guide pulley and a rotational axle 174 for the sixth guide pulley). Each of the guide pulleys is disposed over a respective one of the rotational axles in such a manner that an axis line of the rotational axle is perpendicular to the plane of rotation Gr of the groove of the respective guide pulley. The guide pulleys are rotatably or fixedly mounted on the respectively guide pulley mounts through the respective rotational axles.

Optionally, the wire transmission 1 may further include a rod drive shaft (not shown), and the rod 2 may be rotatably coupled to the base. The rod drive shaft is configured to drive the rod 2 to spin. Preferably, the rod drive shaft is arranged in symmetry with the third end drive shaft 14 with respect to the second plane of symmetry. The rod drive shaft may be, for example, similar in structure to the first end drive shaft 12 and rotatably arranged on the base 11. The rod drive shaft may be provided with a coaxial gear and configured to drive the rod 2 to spin by means of the gear or another transmission element so as to provide one or more additional degrees of freedom to the surgical instrument to allow easier operation and use.

The wire transmission further includes a guide frame base 15 extending parallel to the base 11. The guide frame base 15 is provided with through holes, which correspond in position, and are connected through bearings, respectively to the end drive shafts and the rod drive shaft, in order to prevent the occurrence of lateral oscillation during rotation of one or more of the end drive shafts and the rod drive shaft. The first guide base 17 and the second guide base 16 may be disposed on the guide frame base 15.

In summary, in this embodiment, the fifth traction element 21 and the sixth traction element 24 in the third transmission module are wound on the third end drive shaft 14 in opposite directions, guided toward the rod 2 by the fifth guide pulley 163 and the sixth guide pulley 173, respectively, passed through the rod 2 and then through the fifth through hole 21b and the sixth through hole 24b, respectively, wounded in opposite directions on the first rotational axle 304, and coupled to the effector base 301, so as to be able to drive the effector base 301 to rotate about the first rotational axle 304. The first traction element 23 and the second traction element 25 in the first transmission module are wound on the first end drive shaft 12 in opposite directions, guided toward the rod 2 by the first guide pulley 171 and the second guide pulley 175, respectively, passed through the rod 2 and then through the first through hole 23b and the second through hole 25b, respectively, wounded in opposite directions on the second rotational axle 305, and fixed to the first openable and closable plate member 302, so as to be able to drive the first openable and closable plate member 302 to rotate about the second rotational axle 305. The third traction element 22 and the fourth traction element 26 in the second transmission module are wound on the second end drive shaft 13 in opposite directions, guided toward the rod 2 by the third guide pulley 161 and the fourth guide pulley 165, respectively, passed through the rod 2 and then through the third through hole 22b and the fourth through hole 26b, respectively, wounded in opposite directions on the second rotational axle 305, and fixed to the second openable and closable plate member 303, so as to be able to drive the second openable and closable plate member 303 to rotate about the second rotational axle 305. In addition, the first to sixth guide pulleys are configured so that the projections of the six traction elements are circumferentially arranged in the same manner as the circumferential arrangement of the six through holes at the distal end of the instrument. Further, constrained by the end drive shafts and the entry points of tangency, the traction elements form angles of 0-0.2° with the planes of rotation Gr of the grooves of the respective guide pulleys. Compared with the conventional wire transmission, the wire transmission according to this embodiment requires the use of only six guide pulleys, which are individually configurable. During operation, no direct contact or mutual rubbing will occur among the six traction elements, and angles of deflection of the traction elements from the respective guide pulleys are controlled within 0.2°, resulting in minimal power transmission resistance and high reliability. Further, the six traction elements maintain the same arrangement order both upstream and downstream of the rod 2, avoiding mutual crossing or rubbing among the traction elements within the rod 2.

It is to be understood that in some other embodiments, instead of three, the wire transmission 1 may include other numbers of transmission modules, e.g., two, four or more.

In the first embodiment of the present invention, there is also provided a surgical robot including a mechanical arm and the surgical instrument as defined above. The surgical instrument is disposed at an end of the mechanical arm, and the mechanical arm is configured to adjust the position and/or orientation of the surgical instrument. Since the surgical robot incorporates the above surgical instrument, it has all the benefits of the surgical instrument. The surgical robot may include other components known in the art, which can be appropriately selected and configured by those skilled in the art, and a detailed description thereof is deemed unnecessary and omitted herein.

Embodiment 2

A surgical instrument according to a second embodiment of the present invention is substantially similar to that of Embodiment 1, so only differences between them will be described below.

Figure 14:
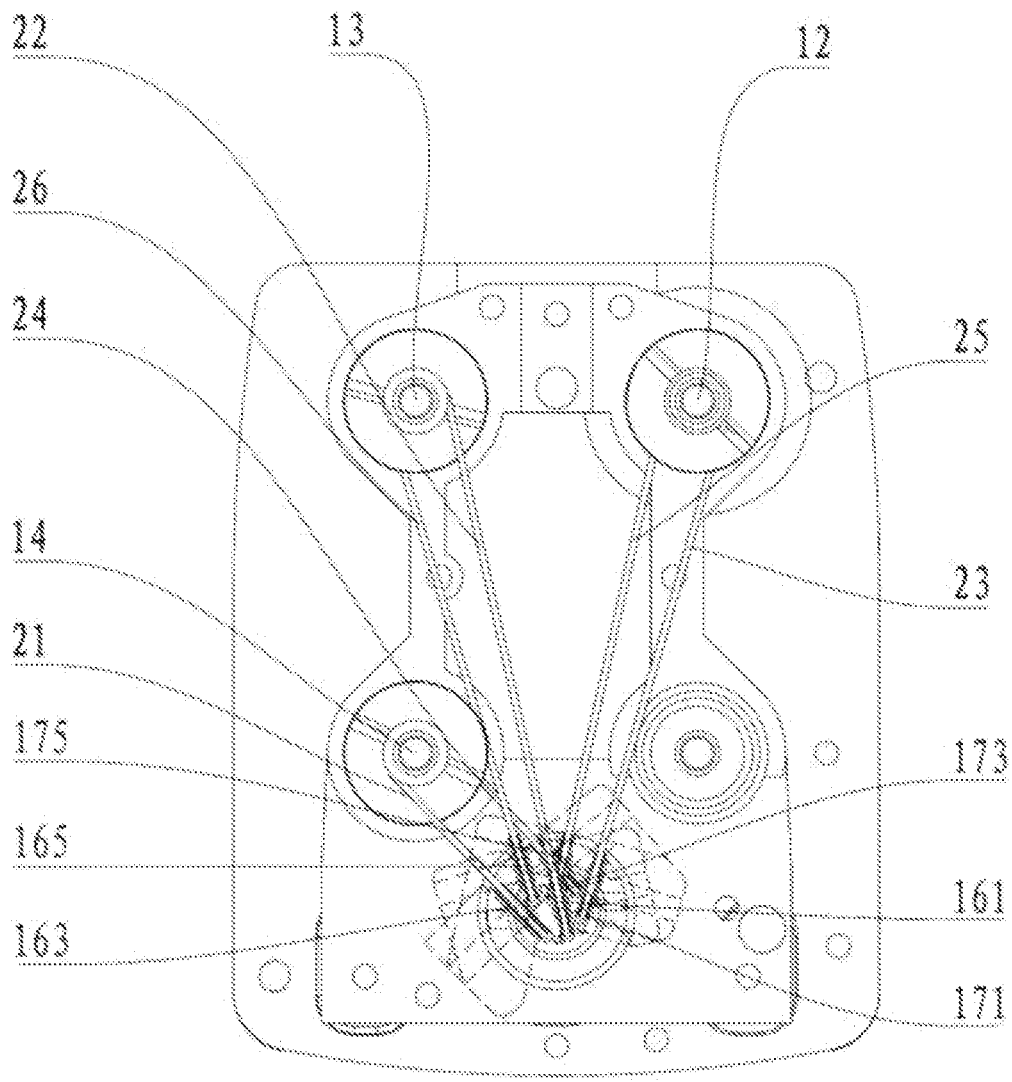
FIG. 14 is a top view of a wire transmission according to a second embodiment of the present invention.
Figure 15:
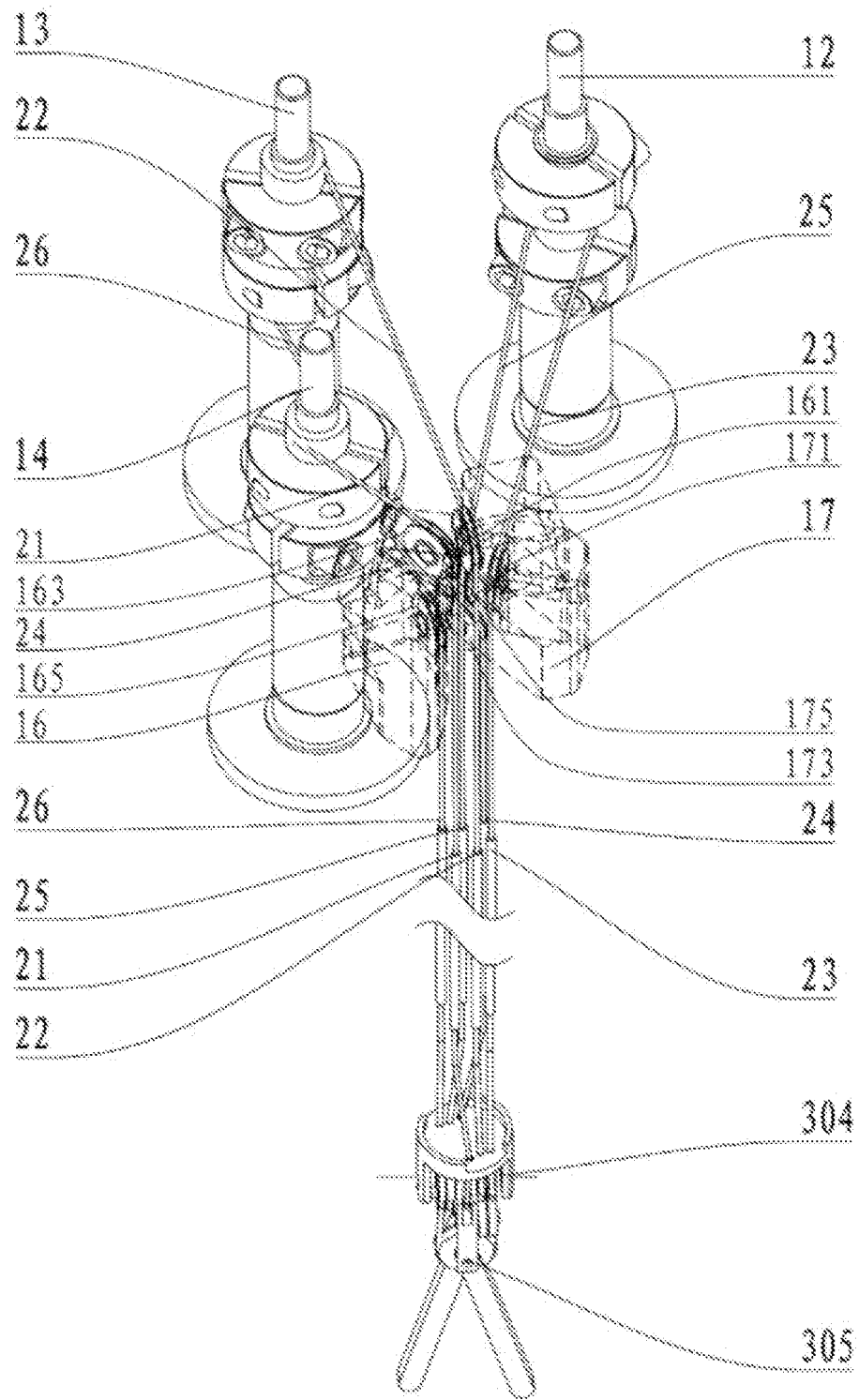
FIG. 15 is a stereoscopic view of the wire transmission according to the second embodiment of the present invention.

Reference is now made to FIGS. 14 and 15. FIG. 14 is a top view of a wire transmission according to the second embodiment of the present invention. FIG. 15 is a stereoscopic view of the wire transmission according to the second embodiment of the present invention.

In the second embodiment, the arrangement of the guide pulleys for the respective traction elements differs from that of Embodiment 1. Specifically, as shown in FIGS. 14 and 15, the third guide pulley 161, the first guide pulley 171 and the sixth guide pulley 173 are disposed on the first guide base 17, while the fifth guide pulley 163, the second guide pulley 175 and the fourth guide pulley 165 are arranged on the second guide base 16. Moreover, the sixth guide pulley 173 is closer to the base 11 than the first guide pulley 171 that is in turn closer to the base 11 than the third guide pulley 161, and the fourth guide pulley 165 is closer to the base 11 than the second guide pulley 175 that is in turn closer to the base 11 than the fifth guide pulley 163. The first 23 to sixth 24 traction elements correspond to the first 171 to sixth 173 guide pulleys, respectively. The arrangement of the end drive shafts and the traction elements is the same as that of Embodiment 1, so a repetitious description thereof is omitted.

It is to be noted that this embodiment is not limited to the above arrangement of the guide pulleys on the guide bases, and alternative arrangements are possible. Those skilled in the art may interchange some of the guide pulleys in position while still achieving the similar results. With the above arrangement of the six guide pulleys, the first segments of the six traction elements can also be made parallel to each other or extend in different planes, thus avoiding the traction elements from coming into contact or abrading against one another.

Embodiment 3

A surgical instrument according to a third embodiment of the present invention is substantially similar to that of Embodiment 1, so only differences between them will be described below.

Figure 16:
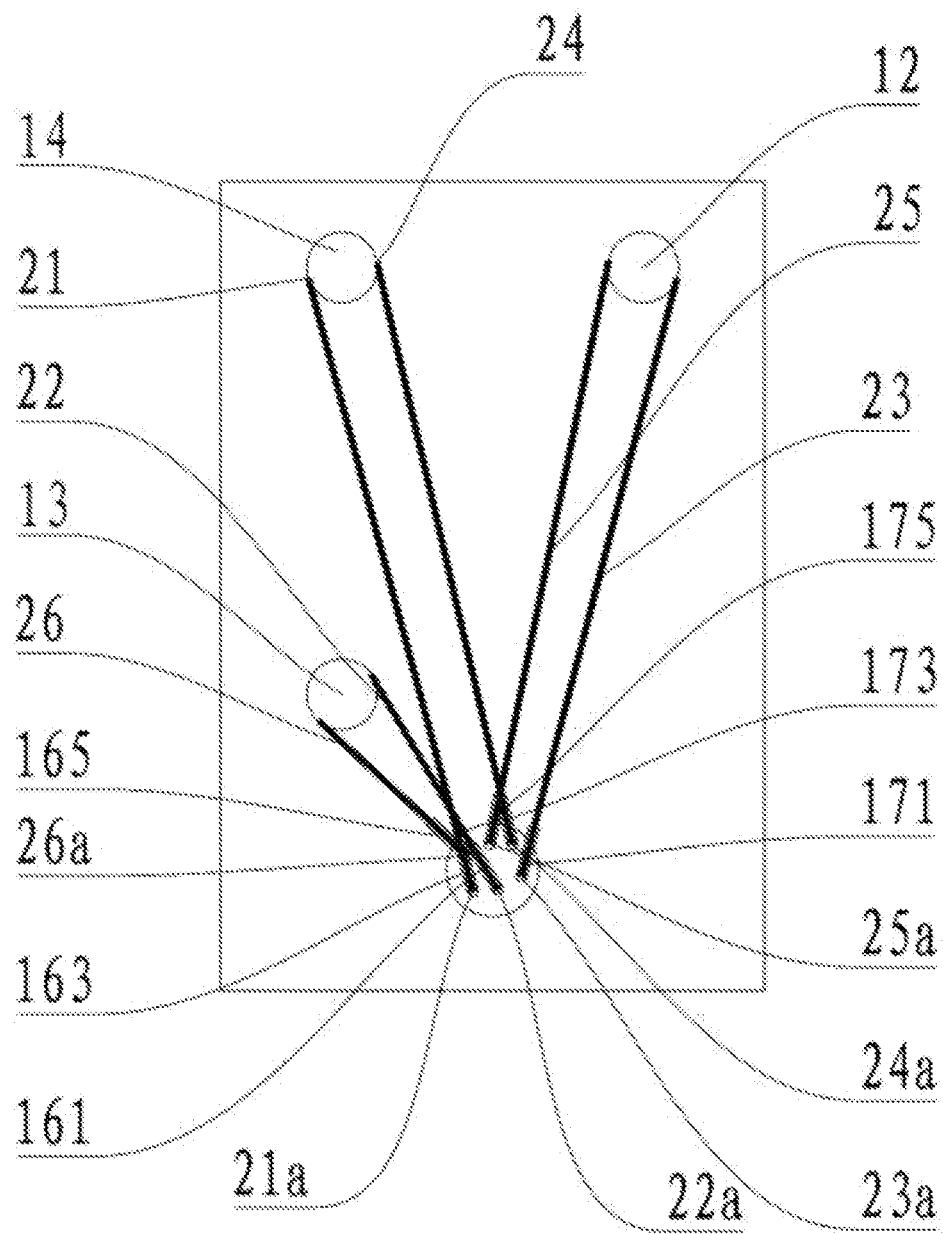
FIG. 16 schematically illustrates a transmission plane of a wire transmission according to a third embodiment of the present invention.

FIG. 16 schematically illustrates a transmission plane of a wire transmission according to the third embodiment of the present invention.

In the third embodiment, the arrangement of the end drive shaft for the respective traction elements differs from that of Embodiment 1. Specifically, as shown in FIG. 16, the third end drive shaft 14 in the third transmission module is farther from the end section than the second end drive shaft 13 in the second transmission module. Moreover, the first end drive shaft 12 in the first transmission module and the third end drive shaft 14 in the third transmission module are arranged in symmetry with respect to the second plane of symmetry, and the second end drive shaft 13 in the second transmission module and the third end drive shaft 14 in the third transmission module are arranged in symmetry with respect to the first plane of symmetry. That is, compared with Embodiment 1, the second end drive shaft 13 is interchanged in position with the third end drive shaft 14. The arrangement of the first 171 to sixth 173 guide pulleys and the traction elements is the same as that of Embodiment 1, so a repetitious description thereof is omitted.

It is to be noted that this embodiment is not limited to the above arrangement of the end drive shafts on the base, and alternative arrangements are also possible. Those skilled in the art may interchange some of the end drive shafts in position while still achieving the similar results.

Embodiment 4

A surgical instrument according to a fourth embodiment of the present invention is substantially similar to that of Embodiment 1, so only differences between them will be described below.

Figure 17:
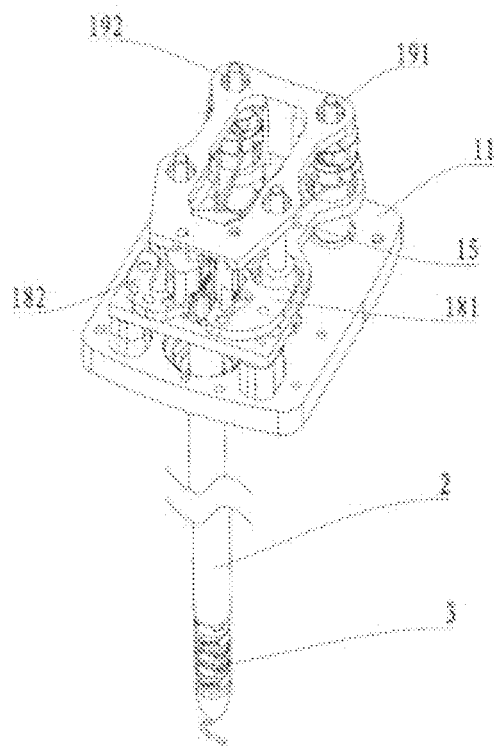
FIG. 17 is a schematic illustration of a surgical instrument according to a fourth embodiment of the present invention.
Figure 18:
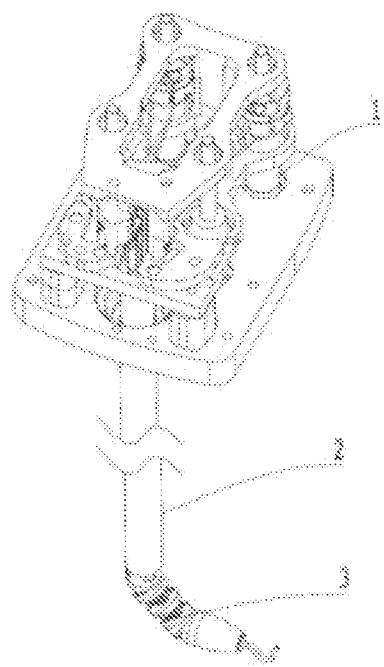
FIG. 18 schematically illustrates swinging of an end section of the surgical instrument of FIG. 17.
Figure 19:
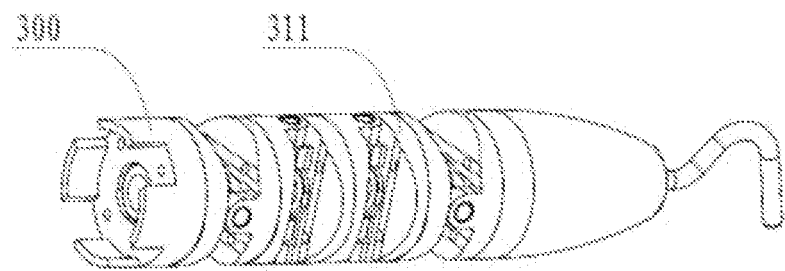
FIG. 19 is a schematic illustration of the end section according to the fourth embodiment of the present invention.
Figure 20:
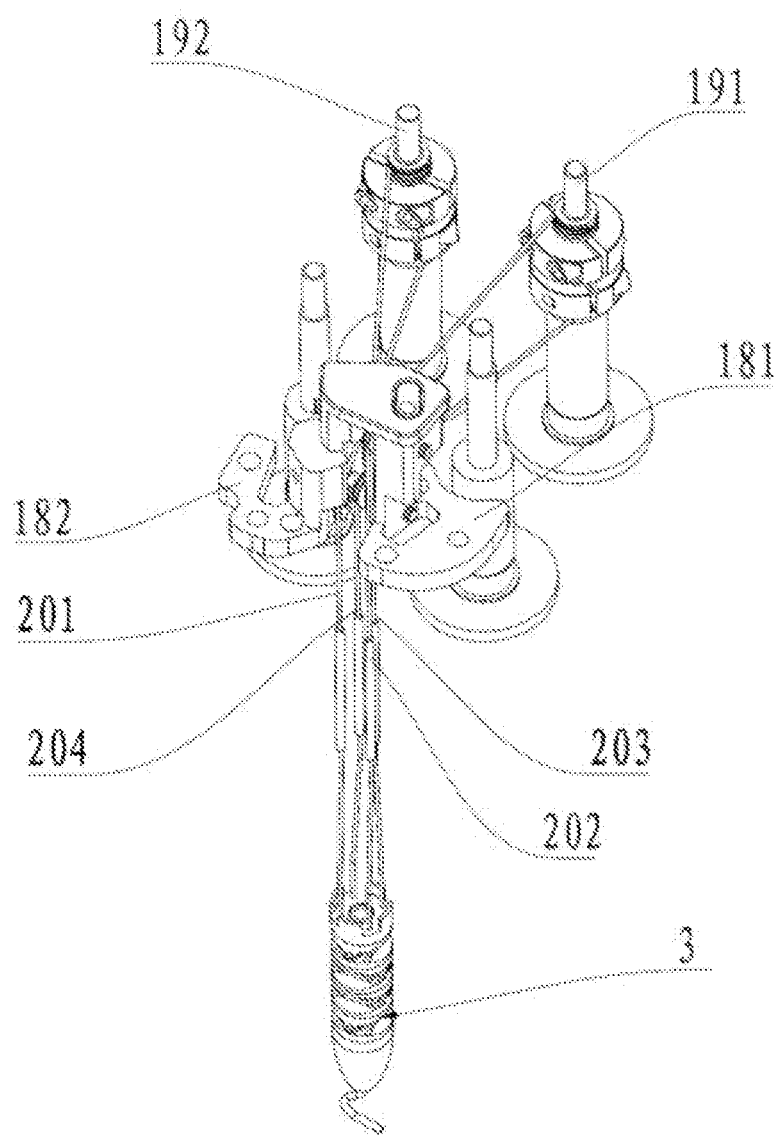
FIG. 20 is a schematic illustration of a wire transmission according to the fourth embodiment of the present invention.
Figure 21:
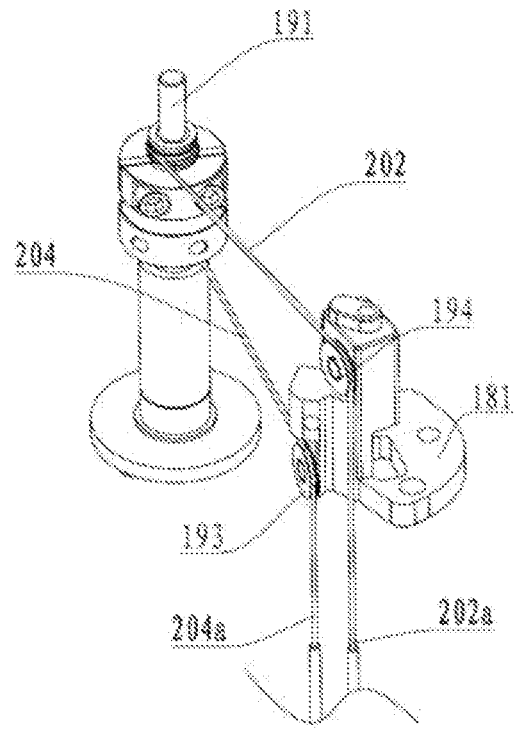
FIG. 21 is a schematic illustration of a fourth transmission module according to the fourth embodiment of the present invention.
Figure 22:
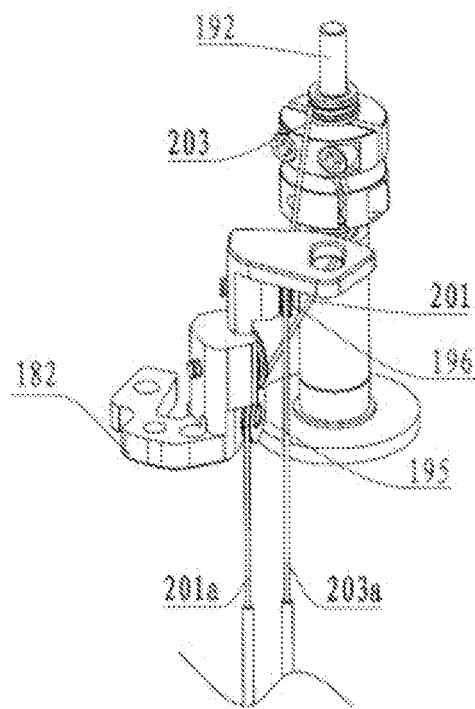
FIG. 22 is a schematic illustration of a fifth transmission module according to the fourth embodiment of the present invention.
Figure 23:
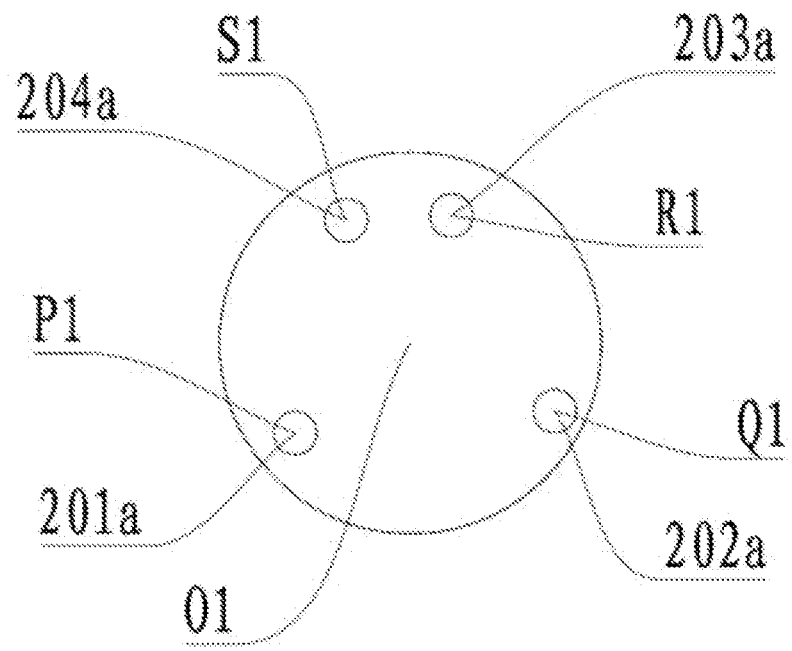
FIG. 23 is a schematic cross-sectional view of a rod at a proximal end thereof according to the fourth embodiment of the present invention.
Figure 24:
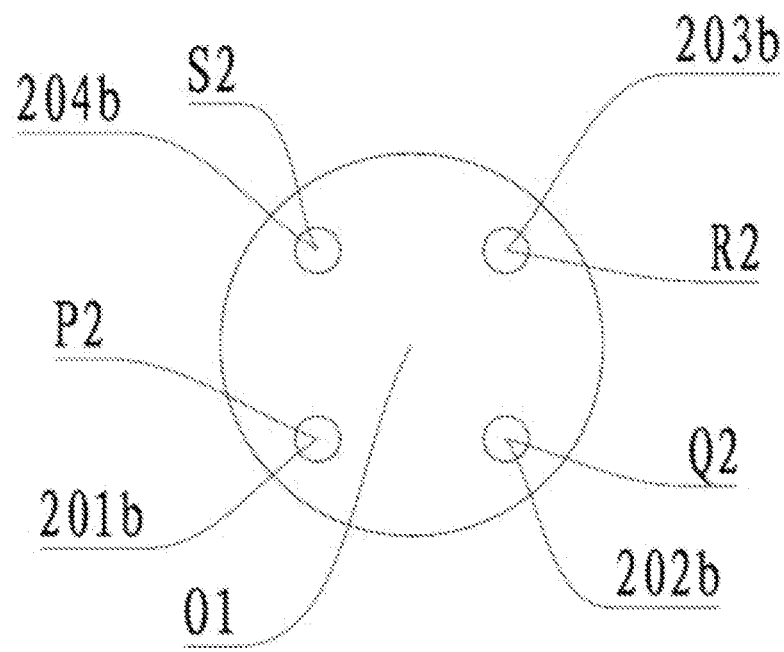
FIG. 24 is a schematic illustration of a proximal end portion of the end section according to the fourth embodiment of the present invention.
Figure 25:
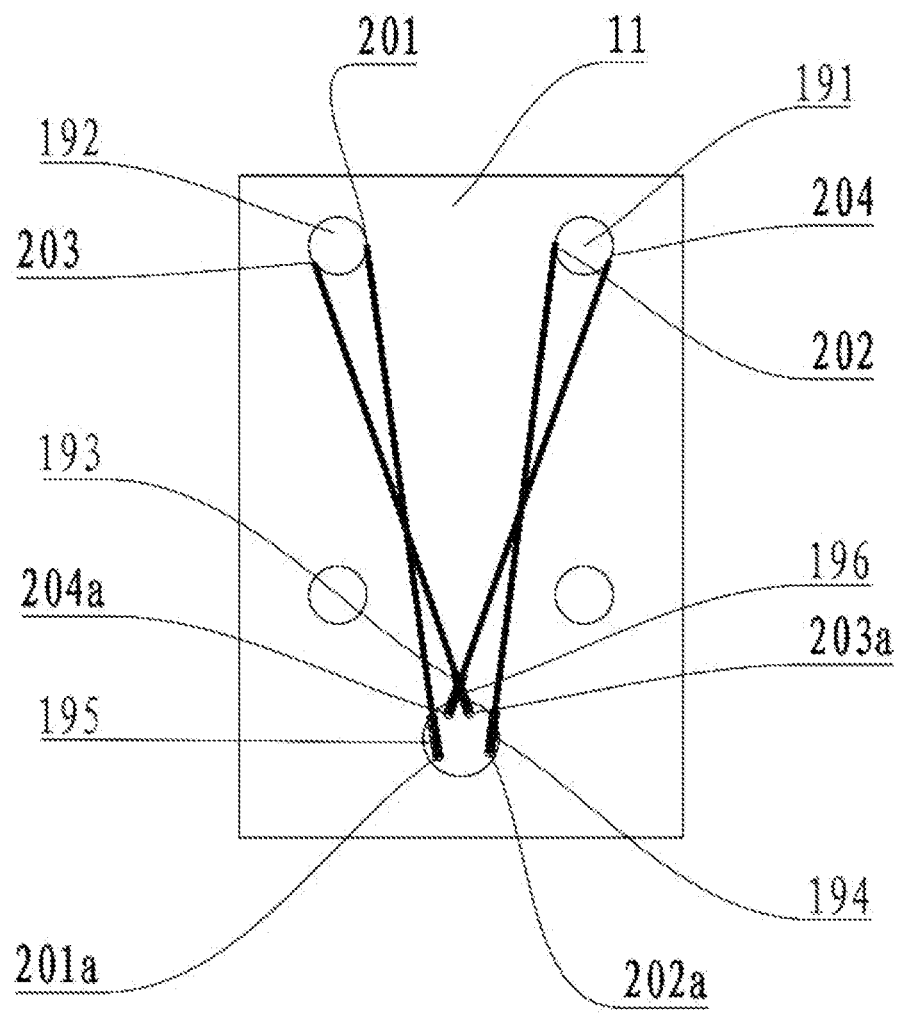
FIG. 25 schematically illustrates a transmission plane of the wire transmission according to the fourth embodiment of the present invention.

Reference is now made to FIGS. 17 to 26(A) and 26(B). FIG. 17 is a schematic illustration of the surgical instrument according to the fourth embodiment of the present invention. FIG. 18 schematically illustrates swinging of an end section of the surgical instrument of FIG. 17. FIG. 19 is a schematic illustration of the end section according to the fourth embodiment of the present invention. FIG. 20 is a schematic illustration of a wire transmission according to the fourth embodiment of the present invention. FIG. 21 is a schematic illustration of a fourth transmission module according to the fourth embodiment of the present invention. FIG. 22 is a schematic illustration of a fifth transmission module according to the fourth embodiment of the present invention. FIG. 23 is a schematic cross-sectional view of a rod at a proximal end thereof according to the fourth embodiment of the present invention. FIG. 24 is a schematic illustration of a proximal end portion of the end section according to the fourth embodiment of the present invention. FIG. 25 schematically illustrates a transmission plane of the wire transmission according to the fourth embodiment of the present invention. FIGS. 26(A) and (B) schematically illustrates the cases where ∠P1O1Q1 is respectively minimum and maximum in the rod's cross-section according to the fourth embodiment of the present invention.

As shown in FIGS. 17 and 18, the fourth embodiment differs from Embodiment 1 in degrees of freedom and the structure of the end section 3 and in the number of transmission modules. Specifically, referring to FIGS. 20 to 22, the end section 3 in the surgical instrument according to the fourth embodiment includes a snake-like robot arm including multiple links 311, which are chained together axially and can swing in at least two directions, thus providing at least two degrees of freedom. For example, the snake-like robot arm may swing around both a third axis line and a fourth axis line. Preferably, the third and fourth axis lines are perpendicular to each other. Accordingly, the end section 3 has at least two degrees of freedom.

The wire transmission 1 in the surgical instrument includes at least two transmission modules. For example, it may include a fourth transmission module and a fifth transmission module. The fourth transmission module includes a fourth end drive shaft 191, a seventh traction element 204, an eighth traction element 202, a seventh guide pulley 193 and an eighth guide pulley 194. The fifth transmission module includes a fifth end drive shaft 192, a ninth traction element 201, a tenth traction element 203, a ninth guide pulley 195 and a tenth guide pulley 196. The seventh, eighth, ninth and tenth traction elements 204, 202, 201 and 203 correspond to the seventh, eighth, ninth and tenth guide pulleys 193, 194, 195 and 196, respectively.

Referring to FIGS. 19 and 20, in an alternative embodiment, the seventh and eighth traction elements 204 and 202 in the fourth transmission module and the ninth and tenth traction elements 201 and 203 in the fifth transmission module are successively passed through the links 311 and then coupled to the most distal link 311. In this way, the snake-like robot arm can be driven by the fourth and fifth transmission modules to swing in two directions, providing two degrees of freedom. For example, the seventh traction element 204 and the eighth traction element 202 may be used to cause the snake-like robot arm to swing around the third axis line, while the ninth traction element 201 and the tenth traction element 203 may be used to cause the snake-like robot arm to swing around the fourth axis line.

Additionally, referring to FIGS. 19 and 24, the proximal end portion 300 may be provided with four circumferentially arranged through holes, i.e., a seventh through hole 204b, a ninth through hole 201b, an eighth through hole 202b and a tenth through hole 203b, which are arranged around the center of the proximal end portion 300 in the order: seventh, ninth, eighth and tenth, in order to constrain extension of the seventh traction element 204, the ninth traction element 201, the eighth traction element 202 and the tenth traction element 203, respectively. Moreover, a center S2 of the seventh through hole 204b and a center Q2 of the eighth through hole 202b may be symmetrical to each other with respect to the center O1 of the proximal end portion 300 (i.e., the projection of the axis line of the end section on the proximal end portion 300), and a center P2 of the ninth through hole 201b and a center R2 of the tenth through hole 203b may be symmetrical to each other with respect to the center of the proximal end portion 300. Preferably, a line connecting the centers of the seventh through hole 204b and the eighth through hole 202b forms an angle of 45° with the fourth axis line, and a line connecting the centers of the ninth through hole 201b and the tenth through hole 203b forms an angle of 45° with the third axis line.

Referring to FIGS. 20, 23 and 25, the seventh guide pulley 193 has a seventh exit point of tangency, the eighth guide pulley 194 has an eighth exit point of tangency, the ninth guide pulley 195 has a ninth exit point of tangency, and the tenth guide pulley 196 has a tenth exit point of tangency. The seventh traction element 204 at the seventh exit point of tangency is projected on the proximal end portion 300 as a seventh projection. The eighth traction element 202 at the eighth exit point of tangency is projected on the proximal end portion 300 as an eighth projection. The ninth traction element 201 at the ninth exit point of tangency is projected on the proximal end portion 300 as a ninth projection. The tenth traction element 203 at the tenth exit point of tangency is projected on the proximal end portion 300 as a tenth projection. The seventh guide pulley 193, the ninth guide pulley 195, the eighth guide pulley 194 and the tenth guide pulley 196 are configured so that the seventh, ninth, eighth and tenth projections are circumferentially arranged in the same order as the circumferential order of the seventh through hole 204b, the ninth through hole 201b, the eighth through hole 202b and the tenth through hole 203b.

Preferably, the surgical instrument further includes a rod 2 configured coaxially with the axis line of the end section. The rod 2 is provided with a through lumen for passage of the traction elements therethrough. The seventh traction element 204, the ninth traction element 201, the eighth traction element 202 and the tenth traction element 203 are all passed through the rod 2 and then coupled to the end section 3. In addition, referring to FIG. 23, the four traction elements all have a diameter of d, and the rod 2 has a diameter of D. Further, the respective projections also all have a diameter of d. A center of the eighth projection of the eighth traction element 202 is located within a circular area, which is centered at a point of symmetry of a center of the seventh projection of the seventh traction element 204 with respect to the axis line and has a radius of 5d. A center of the tenth projection of the tenth traction element 203 is located within a circular area, which is centered at a point of symmetry of a center of the ninth projection of the ninth traction element 201 with respect to the axis line and has a radius of 5d. The projections of any two of the traction elements may be spaced from each other by a center-to-center distance that is greater than d, e.g., 1.1d, 1.2d or 1.3d. The center of the projection of any of the traction elements may be spaced from an inner surface of the rod 2 by a distance that is greater than 0.5d, e.g., 0.6d, 0.7d, 0.8d, 0.9d or d. The projection of any of the traction elements may be spaced from the rod 2 by a center-to-center distance that is greater than 0.5d, e.g., 0.6d, 0.7d, 0.8d, 0.9d or d.

Further, as shown in FIG. 23, if the center of the seventh projection of the seventh traction element 204 is denoted as S1, the projection of the axis line of the end section 3 as O1, the center of the eighth projection of the eighth traction element 202 as Q1, the center of the ninth projection of the ninth traction element 202 as P1, the center of the tenth projection of the tenth traction element 203 as R1 and the internal diameter of the rod 2 as D, then the ninth projection of the ninth traction element 201 and the eighth projection of the eighth traction element 202 satisfy:

$$\angle P1O1Q1 \in \left[2acrsin\left(\frac{0.6d}{0.5D-0.6d}\right), \pi - 2acrsin\left(\frac{0.6d}{0.5D-0.6d}\right)\right].$$

Reference is now made to FIGS. 26(A) and 26(B). FIG. 26(A) schematically illustrates the case where ∠P1O1Q1 is minimum, while FIG. 26(B) schematically illustrates the case where ∠P1O1Q1 is maximum. In these figures, H denotes the farthest point of the ninth projection of the ninth traction element 201 from the projection O1 of the axis line of the end section 3, and I represents a point where the ninth projection of the ninth traction element 201 comes into contact with the eighth projection of the eighth traction element 202. As shown in FIG. 26(A), when ∠P1O1Q1 is minimum, the ninth projection of the ninth traction element 201 is adjacent to the eighth projection of the eighth traction element 202. As shown in FIG. 26(B), when ∠P1O1Q1 is maximum, the tenth projection of the tenth traction element 203 is symmetrical to the ninth projection of the ninth traction element 201 with respect to the center O1 of the rod 2, while the eighth projection of the eighth traction element 202 is adjacent to the tenth projection of the tenth traction element 203. Considering any two of the traction elements will abrade against each other when they come into direct contact, a minimum allowable distance between their projections may be set to 1.2d. So, we obtain:

$$\sin \theta = 1.2*P1I/(O1H-1.2*P1H);$$

$$a = \angle P1O1Q1 = 2\theta;\text{ and}$$

$$P1I = P1H*0.5d, O1H = 0.5D,$$

for the case where a=∠P1O1Q1 is minimum, as shown in FIG. 26(A).
Therefore, $$a = \angle P1O1Q1 = 2\arcsin\left(\frac{0.6d}{0.5D - 0.6d}\right),$$

when a=∠P1O1Q1 is minimum.
Likewise, $$a = \angle P1O1Q1 = \pi - 2\theta = \pi - 2\arcsin\left(\frac{0.6d}{0.5D - 0.6d}\right),$$

when a=∠P1O1Q1 is maximum, as shown in FIG. 26(B).

For the above expressions, D should be large enough to allow the traction elements to be housed within the lumen of the rod 2. With this arrangement, the four traction elements will not come into contact with one another or with the inner surface of the rod 2. As a result, they will encounter less frictional resistance when used to tract the end section 3. Reference can be made to Embodiment 1 for more details in the arrangement of the projections of the four traction elements, so a further detailed thereof is omitted. Preferably, the base 11 is provided thereon with a third guide base 181 and a fourth guide base 182 opposing the third guide base 181. The third guide base 181 is located closer to the fourth end drive shaft 191 than the fourth guide base 182, and the fourth guide base 182 is located closer to the fifth end drive shaft 192 than the third guide base 181. The seventh guide pulley 193 and the eighth guide pulley 194 are both disposed on the third guide base 181, and the ninth guide pulley 195 and the tenth guide pulley 196 are both disposed on the fourth guide base 182. Moreover, the seventh guide pulley 193 is spaced from the base 11 by a distance that is less than a distance from the eighth guide pulley 194 to the base 11, and the ninth guide pulley 195 is spaced from the base 11 by a distance that is less than a distance from the tenth guide pulley 196 to the base 11. Reference can be made to Embodiment 1 for more details in the configurations and structures of the guide bases and guide pulleys, so a further detailed thereof is omitted.

The embodiments disclosed herein are described in a progressive manner, with the description of each embodiment focusing on its differences from others. Reference can be made between the embodiments for their identical or similar features. Additionally, features of different embodiments may be combined with one another, without limiting the scope of the present invention. Further, the several embodiments described above are merely illustrative rather than limitative of the present invention. Those of ordinary skill in the art can make various variations and modifications (e.g., integrating the components on the base into fewer components or split them into more components, changing the relative positions of the end drive shafts, or changing the spatial positions of the guide pulleys), without departing from the spirit of the invention, and all of these variations and modifications are intended to also fall within the scope of the appended claims.

What is claimed is:

1. A surgical instrument, comprising a wire transmission and an end section,
    the wire transmission comprising a base and n transmission modules, each of the transmission modules comprising an end drive shaft, two traction elements and two guide pulleys, where n is a natural number,
    the end section having at least n degrees of freedom, the end section comprising a proximal end portion provided with 2n circumferentially arranged through holes,
    each of the end drive shafts rotatably disposed on the base and configured to drive the end section to move via each of the two traction elements,
    in an $i^{th}$ one of the transmission modules, $j^{th}$ and $(j+1)^{th}$ traction elements of the two traction elements are proximally wound on an $i^{th}$ end drive shaft of at least one of the end drive shafts in opposite directions relative to each other, the $j^{th}$ and $(j+1)^{th}$ traction elements distally guided by $j^{th}$ and $(j+1)^{th}$ guide pulleys of the two guide pulleys toward $j^{th}$ and $(j+1)^{th}$ ones of the through holes, respectively, and then passed through the $j^{th}$ and $(j+1)^{th}$ through holes, respectively, where i is a natural number in a range from 1 to n, and j=2i−1,
    each of the guide pulleys comprising a groove for receiving therein a respective one of the traction elements, each of the grooves having a plane of rotation, an entry point of tangency and an exit point of tangency, the respective one of the traction elements configured to enter each of the guide pulleys at the respective entry point of tangency and leave each of the guide pulleys at the respective exit point of tangency, each of the guide pulleys configured so that an angle between the respective plane of rotation and the respective one of the traction elements defined by at least one of the end drive shafts and the respective entry point of tangency is in a range of 0-0.2°, projections of each of the traction elements at the respective exit points of tangency on the proximal end portion circumferentially arranged in a same order as a circumferential arrangement of the respective through holes on the proximal end portion.

2. The surgical instrument of claim 1, wherein the end section further has an axis line extending from a proximal end to a distal end thereof, and wherein each of the guide pulleys is further configured so that an angle between the axis line and the respective one of the traction elements defined by the respective exit point of tangency and the respective one of the through holes is in a range of 0-5°.

3. The surgical instrument of claim 1, wherein each of the guide pulleys is further configured so that the angle between an axis line and the respective one of the traction elements defined by the respective exit point of tangency and the respective one of the through holes is in a range of 0-1.5°.

4. The surgical instrument of claim 1, wherein the $i^{th}$ end drive shaft is connected to the $j^{th}$ traction element at a $j^{th}$ junction, and the respective one of the traction elements between the $j^{th}$ junction and the respective entry point of tangency of the $j^{th}$ guide pulley forms an angle in a range of 0-10° with the base, and wherein the $i^{th}$ end drive shaft is connected to the $(j+1)^{th}$ traction element at a $(j+1)^{th}$ junction, and the respective one of the traction elements between the $(j+1)^{th}$ junction and the respective entry point of tangency of the $(j+1)^{th}$ guide pulley forms an angle in a range of 0-10° with the base;

wherein at least two of the traction elements extend parallel to each other or in different planes between the respective junction of the $j^{th}$ junction or the $(j+1)^{th}$ junction and the respective entry points of tangency.

5. The surgical instrument of claim 1, further comprising a rod drive shaft and a rod, the rod detachably or fixedly coupled to the end section, the rod drive shaft configured to drive the rod to spin.

6. The surgical instrument of claim 1, wherein the at least n degrees of freedom includes at least three degrees of freedom, and wherein the n transmission modules comprises a first transmission module, a second transmission module and a third transmission module, each of the first, second and third transmission modules configured to drive the end section to move in a respective one of the at least n degrees of freedom, the first transmission module comprising a first end drive shaft of the end drive shafts, a first traction element and a second traction element of the traction elements, a first guide pulley and a second guide pulley of the guide pulleys, the second transmission module comprising a second end drive shaft of the end drive shafts, a third traction element and a fourth traction element of the traction elements, a third guide pulley and a fourth guide pulley of the guide pulleys, the third transmission module comprising a third end drive shaft of the end drive shafts, a fifth traction element and a sixth traction element of the traction elements, a fifth guide pulley and a sixth guide pulley of the guide pulleys, the first, second, third, fourth, fifth and sixth traction elements corresponding to the first, second, third, fourth, fifth and sixth guide pulleys, respectively.

7. The surgical instrument of claim 6, wherein the end section further comprises an end effector, the end effector comprising an effector base, a first openable and closable plate member and a second openable and closable plate member, the first and second openable and closable plate members both rotatably coupled to the effector base and thus providing at least two degrees of opening and closing freedom, the effector base rotatably coupled to the proximal end portion and thus providing at least one degree of swing freedom, and wherein the first transmission module is configured to drive the first openable and closable plate member to move, the second transmission module is configured to drive the second openable and closable plate member to move, and the third transmission module is configured to drive the effector base to move relative to the proximal end portion;

wherein the through holes on the proximal end portion comprise a first through hole, a second through hole, a third through hole, a fourth through hole, a fifth through hole and a sixth through hole for constraining extension of the first traction element, the second traction element, the third traction element, the fourth traction element, the fifth traction element and the sixth traction element, respectively, wherein an axis of rotation of the first and second openable and closable plate members is not parallel to an axis of rotation of the effector base, and wherein the fifth through hole, the third through hole, the first through hole, the sixth through hole, the second through hole and the fourth through hole are circumferentially arranged around a center of the proximal end portion;

wherein the fifth through hole is symmetrical to the sixth through hole with respect to the center of the proximal end portion, the third through hole is symmetrical to the second through hole with respect to the center of the proximal end portion, and the first through hole is symmetrical to the fourth through hole with respect to the center of the proximal end portion.

8. The surgical instrument of claim 6, wherein the exit points of tangency include a first exit point of tangency, a second exit point of tangency, a third exit point of tangency, a fourth exit point of tangency, a fifth exit point of tangency and a sixth exit point of tangency, respectively, wherein the first traction element is projected at the first exit point of tangency onto the proximal end portion as a first projection of the projections, the second traction element is projected at the second exit point of tangency onto the proximal end portion as a second projection of the projections, the third traction element is projected at the third exit point of tangency onto the proximal end portion as a third projection of the projections, the fourth traction element is projected at the fourth exit point of tangency onto the proximal end portion as a fourth projection of the projections, the fifth traction element is projected at the fifth exit point of tangency onto the proximal end portion as a fifth projection of the projections, and the sixth traction element is projected at the sixth exit point of tangency onto the proximal end portion as a sixth projection of the projections, wherein the first, second, third, fourth, fifth and sixth projections are circumferentially arranged in a same order as the circumferential arrangement of the respective through holes on the proximal end portion.

9. The surgical instrument of claim 8, wherein the end section further has an axis line extending from a proximal end to a distal end thereof, wherein the first-sixth traction elements all have a diameter of d, and wherein at least one of the projections of the traction elements on the proximal end portion are configured so that a center of the sixth projection is located within a circular area, which is centered at a point of symmetry of a center of the fifth projection with respect to the axis line and has a radius of 5d, a center of the second projection is located within a circular area, which is centered at a point of symmetry of a center of the third projection with respect to the axis line and has a radius of 5d, and a center of the fourth projection is located within a circular area, which is centered at a point of symmetry of a center of the first projection with respect to the axis line and has a radius of 5d.

10. The surgical instrument of claim 9, further comprising a rod configured coaxially with the axis line, the rod provided with a through lumen for passage of the first, second, third, fourth, fifth and sixth traction elements therethrough, and wherein all the traction elements within the rod are configured so that any two of the first-sixth projections are spaced from each other by a center-to-center distance greater than d, that the center of any of the first-sixth projections is spaced from an inner surface of the rod by a distance greater than 0.6d, and that any of the projections is spaced from the rod by a center-to-center distance greater than 0.5d.

11. The surgical instrument of claim 9, further comprising a rod configured coaxially with the axis line, the rod provided with a through lumen for passage of the first, second, third, fourth, fifth and sixth traction elements therethrough, wherein if the center of the fifth projection is denoted as A1, a projection of an axis line of the rod is denoted as O1, the center of the third projection is denoted as B1, the center of the first projection is denoted as C1 and an internal diameter of the rod is denoted as D, then the third and first projections satisfy:

$$\angle A1O1B1 \in \left[2\arcsin\left(\frac{0.6d}{0.5D-0.6d}\right), \pi - 4\arcsin\left(\frac{0.6d}{0.5D-0.6d}\right)\right]; \text{ and}$$

$$\angle A1O1C1 \in \left[4\arcsin\left(\frac{0.6d}{0.5D-0.6d}\right), \pi - 2\arcsin\left(\frac{0.6d}{0.5D-0.6d}\right)\right].$$

12. The surgical instrument of claim 6, wherein the base is provided thereon with a first guide base and an opposing second guide base, and wherein at least three of the first, second, third, fourth, fifth and sixth guide pulleys are disposed on the first guide base and the remaining three of the first, second, third, fourth, fifth and sixth guide pulleys are disposed on the second guide base.

13. The surgical instrument of claim 12, wherein the first, sixth and second guide pulleys are disposed on the first guide base, and the third, fifth and fourth guide pulleys are disposed on the second guide base, so that the second guide pulley is closer to the base than the sixth guide pulley that is in turn closer to the base than the first guide pulley and that the fourth guide pulley is closer to the base than the fifth guide pulley that is in turn closer to the base than the third guide pulley; or wherein the third, first and sixth guide pulleys are disposed on the first guide base, and the fifth, second and fourth guide pulleys are disposed on the second guide base, so that the sixth guide pulley is closer to the base than the first guide pulley that is in turn closer to the base than the third guide pulley and that the fourth guide pulley is closer to the base than the second guide pulley that is in turn closer to the base than the fifth guide pulley.

14. The surgical instrument of claim 6, wherein the end section further has an axis line extending from a proximal end to a distal end thereof, wherein the base has a first plane of symmetry and a second plane of symmetry perpendicular to the first plane of symmetry, the first plane of symmetry intersecting the second plane of symmetry along a line that is parallel to or collinear with the axis line, wherein the second end drive shaft is symmetrical to the third end drive shaft with respect to the first plane of symmetry, wherein the first end drive shaft is symmetrical to the second end drive shaft with respect to the second plane of symmetry, and wherein the second end drive shaft is farther away from the axis line than the third end drive shaft; or wherein the end section further has an axis line extending from a proximal end to a distal end thereof, wherein the base has a first plane of symmetry and a second plane of symmetry perpendicular to the first plane of symmetry, the first plane of symmetry intersecting the second plane of symmetry along a line that is parallel to or collinear with the axis line, wherein the second end drive shaft is symmetrical to the third end drive shaft with respect to the first plane of symmetry, wherein the first end drive shaft is symmetrical to the third end drive shaft with respect to the second plane of symmetry, and wherein the third end drive shaft is farther away from the axis line than the second end drive shaft.

15. The surgical instrument of claim 1, wherein the at least n degrees of freedom includes at least two degrees of freedom, and wherein the n transmission modules comprises a fourth transmission module and a fifth transmission module, each of the fourth and fifth transmission modules configured to drive the end section to move in a respective one of the at least n degrees of freedom, the fourth transmission module comprising a fourth end drive shaft of the end drive shafts, a seventh traction element and an eighth traction element of the traction elements, a seventh guide pulley and an eighth guide pulley of the guide pulleys, the fifth transmission module comprising a fifth end drive shaft of the end drive shafts, a ninth traction element and a tenth traction element of the traction elements, a ninth guide pulley and a tenth guide pulley of the guide pulleys, the seventh, eighth, ninth and tenth traction elements corresponding to the seventh, eighth, ninth and tenth guide pulleys, respectively.

16. The surgical instrument of claim 15, wherein the end section further comprises a robot arm comprising a plurality of links, which are chained together axially and able to swing in at least two directions, thereby providing at least two degrees of freedom, wherein the seventh, eighth, ninth and tenth traction elements are passed through the plurality of links successively and coupled to a most distal one of the plurality of links, and wherein the fourth and fifth transmission modules are configured to drive the robot arm to swing in the at least two directions;

wherein the through holes on the proximal end portion comprise a seventh through hole, an eighth through hole, a ninth through hole and a tenth through hole for constraining extension of the seventh traction element, the eighth traction element, the ninth traction element and the tenth traction element, respectively, and wherein the seventh, ninth, eighth and tenth through holes are arranged circumferentially on the proximal end portion;

wherein the seventh through hole is symmetrical to the eighth through hole with respect to a center of the proximal end portion, and the ninth through hole is symmetrical to the tenth through hole with respect to the center of the proximal end portion.

17. The surgical instrument of claim 15, wherein the seventh guide pulley, the eighth guide pulley, the ninth guide pulley and the tenth guide pulley have a seventh exit point of tangency, an eighth exit point of tangency, a ninth exit point of tangency and a tenth exit point of tangency, respectively, of the exit points of tangency, wherein the seventh traction element is projected at the seventh exit point of tangency onto the proximal end portion as a seventh projection of the projections, the eighth traction element is projected at the eighth exit point of tangency onto the proximal end portion as an eighth projection of the projections, the ninth traction element is projected at the ninth exit point of tangency onto the proximal end portion as a ninth projection of the projections, the tenth traction element is projected at the tenth exit point of tangency onto the proximal end portion as a tenth projection of the projections, wherein the seventh, eighth, ninth and tenth projections are circumferentially arranged in a same order as the circumferential arrangement of the respective through holes on the proximal end portion;

wherein the end section further has an axis line extending from a proximal end to a distal end thereof, wherein the seventh, eighth, ninth and tenth traction elements all have a diameter of d, and wherein at least one of the seventh, eighth, ninth and tenth projection of the traction elements on the proximal end portion are configured so that a center of the eighth projection is located within a circular area, which is centered at a point of symmetry of a center of the seventh projection with respect to the axis line and has a radius of 5d, and a center of the tenth projection is located within a circular area, which is centered at a point of symmetry of a center of the ninth projection with respect to the axis line and has a radius of 5d.

18. The surgical instrument of claim 17, further comprising a rod configured coaxially with the axis line, the rod provided with a through lumen for passage of at least one of the traction elements therethrough, and wherein all the traction elements within the rod are configured so that any two of the seventh, eighth, ninth and tenth projections are spaced from each other by a center-to-center distance greater than d, that a center of any of the projections is spaced from an inner surface of the rod by a distance greater than 0.6d, and that any of the seventh, eighth, ninth and tenth projections is spaced from the rod by a center-to-center distance greater than 0.5d; or further comprising a rod configured coaxially with the axis line, the rod provided with a through lumen for passage of at least one of the traction elements therethrough, wherein if a projection of an axis line of the rod is denoted as O1, the center of the eighth projection as Q1, the center of the ninth projection as P1 and an internal diameter of the rod as D, then the ninth and eighth projections satisfy:

$$\angle P1O1Q1 \in \left[ 2acrsin\left(\frac{0.6d}{0.5D-0.6d}\right), \pi - 2acrsin\left(\frac{0.6d}{0.5D-0.6d}\right) \right].$$

19. The surgical instrument of claim 15, wherein the base is provided thereon with a third guide base and an opposing fourth guide base, and wherein the seventh and eighth guide pulleys are disposed on the third guide base and the ninth and tenth guide pulleys are disposed on the fourth guide base so that the seventh guide pulley is closer to the base than the eighth guide pulley and that the ninth guide pulley is closer to the base than the tenth guide pulley.

20. A surgical robot, comprising a mechanical arm and the surgical instrument of claim 1, the surgical instrument disposed at an end of the mechanical arm, the mechanical arm configured to adjust a position and/or orientation of the surgical instrument.

* * * * *